(12) United States Patent
Kayser et al.

(10) Patent No.: US 12,430,751 B2
(45) Date of Patent: Sep. 30, 2025

(54) WOUND HEALING ANALYSIS AND TRACKING

(71) Applicant: Hill-Rom Services, Inc., Batesville, IN (US)

(72) Inventors: Susan A. Kayser, Batesville, IN (US); Jennifer Marie Rizzo, Guilford, IN (US); Mary L Pfeffer, Mount Pleasant, SC (US); Jie Zhou, Batesville, IN (US); Nuno M Azeredo, Chicago, IL (US); Marion Le Gall, Vannes (FR)

(73) Assignee: Hill-Rom Services, Inc., Batesville, IN (US)

( * ) Notice: Subject to any disclaimer, the term of this patent is extended or adjusted under 35 U.S.C. 154(b) by 445 days.

(21) Appl. No.: 17/494,091

(22) Filed: Oct. 5, 2021

(65) Prior Publication Data
US 2022/0108447 A1   Apr. 7, 2022

Related U.S. Application Data

(60) Provisional application No. 63/087,605, filed on Oct. 5, 2020.

(51) Int. Cl.
*G16H 40/67* (2018.01)
*A61B 5/00* (2006.01)
(Continued)

(52) U.S. Cl.
CPC ............ *G06T 7/0012* (2013.01); *A61B 5/445* (2013.01); *G16H 10/60* (2018.01);
(Continued)

(58) Field of Classification Search
USPC ............... 378/1–87; 382/100–224, 276–308; 600/300–348, 371, 481–490; 704/1–275;
(Continued)

(56) References Cited

U.S. PATENT DOCUMENTS 8,595,026 B2 * 11/2013 Cellura .................. G16H 40/67
705/2
2015/0150457 A1    6/2015 Wu
(Continued)

FOREIGN PATENT DOCUMENTS

CN           110895968 A       3/2020

OTHER PUBLICATIONS

Ito Takeshi; Endoscope Device and Endoscope Device Operation Method; Jan. 16, 2020 (Year: 2020).*
(Continued)

*Primary Examiner* — Marcellus J Augustin
(74) *Attorney, Agent, or Firm* — Lee & Hayes, P.C.

(57) ABSTRACT

This disclosure is directed towards a patient management system for analyzing images of wounds and tracking the progression of wounds over time. In some examples, a computing device of the patient management system receives an image, and determines that the image depicts a wound. The computing device inputs the image into a machine-learned model trained to classify wounds, and receives, from the machine-learned model, a classification of the wound. The computing device may then display the classification of the wound in a user interface. Additionally, the patient management system may train a machine-learned model to classify wounds.

20 Claims, 11 Drawing Sheets

(51) Int. Cl.
   *A61B 5/103* (2006.01)
   *G06T 7/00* (2017.01)
   *G16H 10/60* (2018.01)

(52) U.S. Cl.
   CPC ............... *G06T 2207/10016* (2013.01); *G06T 2207/20081* (2013.01); *G06T 2207/20084* (2013.01); *G06T 2207/30088* (2013.01)

(58) Field of Classification Search
   USPC ........................................ 706/1–62, 900–903
   See application file for complete search history.

(56) References Cited

U.S. PATENT DOCUMENTS

| | | | | |
|---|---|---|---|---|
| 2017/0076446 | A1* | 3/2017 | Pedersen | G06T 7/194 |
| 2018/0028079 | A1* | 2/2018 | Gurevich | A61B 5/7232 |
| 2018/0055440 | A1* | 3/2018 | Ming | G06V 40/10 |
| 2018/0098727 | A1* | 4/2018 | Spahn | G06T 7/0012 |
| 2019/0125248 | A1* | 5/2019 | Curtin | A61B 5/1455 |
| 2020/0193597 | A1* | 6/2020 | Fan | A61B 5/7275 |
| 2021/0343017 | A1* | 11/2021 | Jordan | G06T 7/0016 |
| 2022/0101996 | A1* | 3/2022 | Iwata | G16H 50/20 |
| 2023/0051436 | A1* | 2/2023 | Ahmad | G06T 7/0016 |
| 2023/0368910 | A1* | 11/2023 | Katra | G16H 15/00 |
| 2024/0257973 | A1* | 8/2024 | Van Hooser | G16H 50/70 |

OTHER PUBLICATIONS

Baker Brett Hugh; Bismuth-Thiol Compositions and Methods for Treating Wounds; Feb. 6, 2020 (Year: 2020).*

Curtin Candice Ganey; Systems and Methods for Classification and Treatment of Decubitus Ulcers; 2017 (Year: 2017).*

Anisuzzaman, et al, "Image Based Artificial Intelligence in Wound Assessment: A Systematic Review", Arxiv.org, Cornell University Library, Sep. 15, 2020, pp. 6-13.

Extended European Search Report mailed Feb. 3, 2022 for European Patent Application No. 21200762.9, 31 pages.

European Office Action mailed Feb. 27, 2024 for European Application No. 21200762.9, a foreign counterpart to U.S. Appl. No. 17/494,091, 8 pages.

Zahia, et al, "Pressure injury image analysis with machine learning techniques: A systematic review on previous and possible future methods", Artificial Intelligence in Medicine, vol. 102, Nov. 13, 2019, pp. 13-20.

* cited by examiner

WOUND HEALING ANALYSIS AND TRACKING

CROSS-REFERENCE TO RELATED APPLICATION

This application is a U.S. Nonprovisional Application of, and claims priority to, U.S. Provisional Application No. 63/087,605, filed Oct. 5, 2020, the entire disclosure of which is incorporated herein by reference.

TECHNICAL FIELD

This application is directed to a patient management system, and in particular, at least systems, devices, and methods, which are utilized and/or configured to analyze images of wounds and track the progression of wounds over time.

BACKGROUND

When a patient incurs or develops a wound, treatment of the wound may require coordination between multiple different individuals, such as healthcare providers (e.g., bedside nurses, wound ostomy continence nurses (WOCs), physicians, surgeons, etc.), the patient, relatives or friends of the patient, and so forth. Conventional healthcare systems often rely on either verbal communication between these individuals to manage treatment of the wound, and/or computing systems designed for generic medical information sharing. These conventional healthcare systems leave gaps when transferring critical information about the wound and sharing how the wound is progressing. For example, bedside nurses, the patient, and relatives or friends of the patient who are caring for the patient often do not have background knowledge of wound care to determine treatment techniques or when a WOC is needed to evaluate the wound. Additionally, conventional healthcare computing systems do not provide options for healthcare providers, the patient, and/or relatives or friends of the patient to track progress of the wound over time, such as whether the wound is healing or not.

The various example embodiments of the present disclosure are directed toward overcoming one or more of the deficiencies associated with existing patient management systems.

SUMMARY

Broadly, the systems and methods disclosed and contemplated herein are directed towards a patient management system for analyzing images of wounds and tracking the progression of wounds over time. Throughout this disclosure, the term "machine-learned model" or "machine learned model" shall refer to a machine learning model, or models, that have at least gone through one iteration of training and/or prediction. In some examples, a computing device of the patient management system receives an image, and determines that the image depicts a wound. The computing device inputs the image into a machine-learned model trained to classify wounds, and receives, from the machine-learned model, a classification of the wound based on training data. Additionally, the computing device may then train the machine-learned model by identifying relationships between the image and at least a portion of the training data. The computing device may then display the classification of the wound in a user interface.

In some examples, a computing device determines, based at least in part on images depicting a wound over a time period, a progression of the wound over the time period. The computing device may receive an image depicting the wound, input at least a portion of the image into a machine-learned model, and receive, from the machine-learned model, a predicted progression of the wound over the time period. In examples, the computing device determines a difference between the predicted progression of the wound over the time period and the progression of the wound over the time period. The computing device may alter one or more parameters of the machine-learned model to minimize the difference.

In some examples, a system includes a camera, a display, one or more processors, and one or more computer-readable media storing instructions that, when executed by the one or more processors, cause the one or more processors to perform operations. For instance, the one or more processors may receive a selection of a body part type in a user interface, and receive a feed from the camera. In examples, the one or more processors cause an outline of the body part type to be displayed over the feed on the display, then capture an image of the feed. The one or more processors may determine that the image depicts a body part of the body part type associated with the outline and determine a size of the body part from the image and associated with the outline. In some examples, the one or more processors determine that the image depicts a wound, a classification of the wound, and determines a characteristic of the wound depicted in the image based at least in part on the size of the body part as depicted in the image.

DETAILED DESCRIPTION

Figure 1:
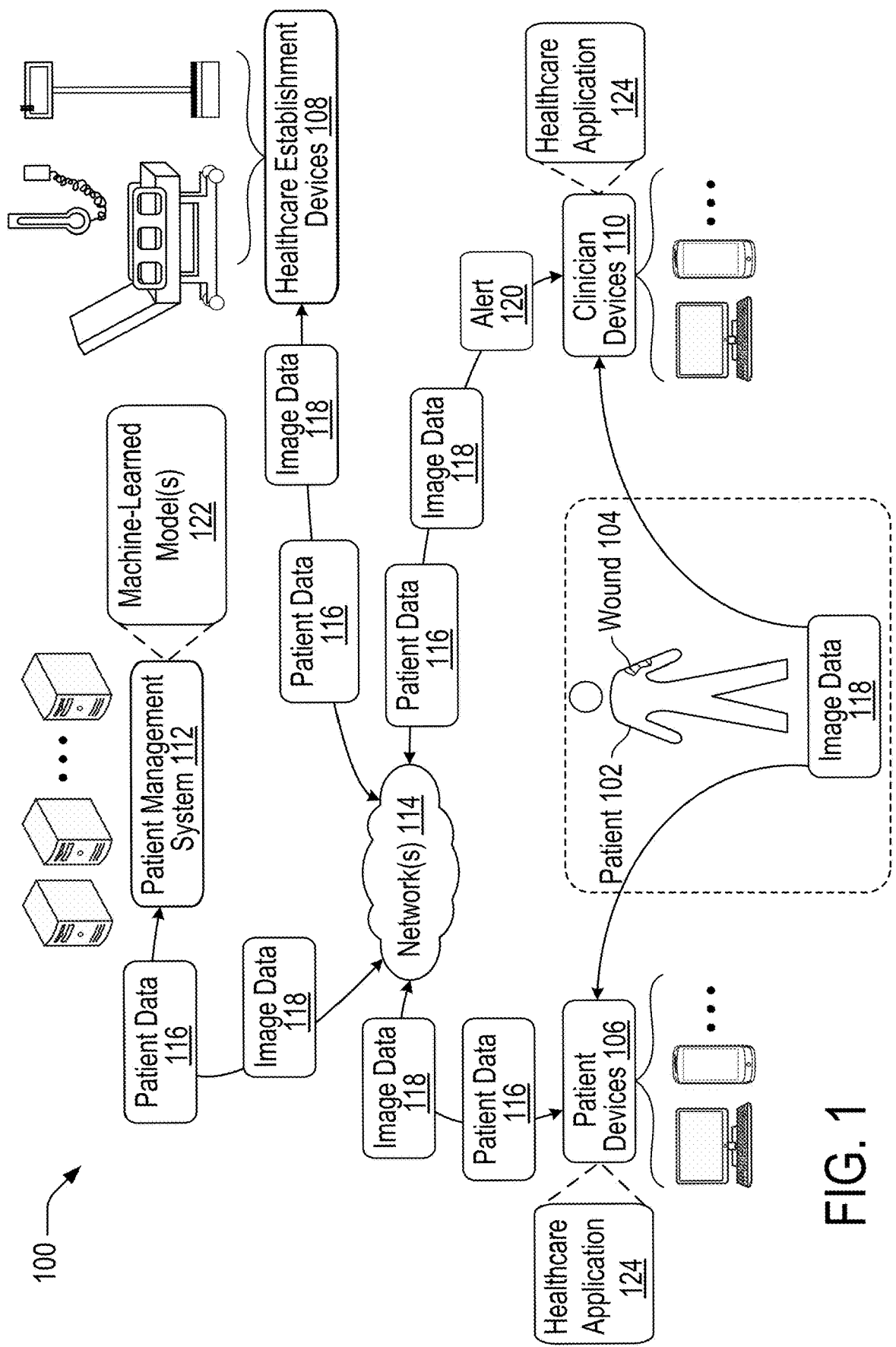
FIG. 1 shows a schematic block diagram of an example patient management system environment, in accordance with examples of the disclosure.

Various embodiments of the present disclosure will be described in detail with reference to the drawings, wherein like reference numerals represent like parts and assemblies throughout the several views. Additionally, any examples set forth in this specification are not intended to be limiting and merely set forth some of the many possible embodiments.

FIG. 1 shows a schematic block diagram of an example patient management system environment 100. The example patient management system environment 100 includes a patient 102 having a wound 104, one or more patient devices 106, one or more healthcare establishment devices 108, one or more clinician devices 110, and a patient management system 112. The patient devices 106, the healthcare establishment devices 108, the clinician devices 110, and/or the patient management system 112 may be in communication via one or more networks 114.

In some examples, the healthcare establishment devices 108 may include devices that generally exist in a healthcare establishment (e.g., physician's office, hospital, clinic, dentist's office, pharmacy, ambulance, and the like) that may impact and/or monitor the health of the patient 102. For instance, the healthcare establishment devices 108 may include blood pressure devices, SpO$_2$ devices, temperature devices, respiratory devices, bodyweight scales, otoscopes, ophthalmoscopes, stethoscopes, vision screening devices, hearing screening devices, microscopes, ECG devices, beds and other furniture, and so on. While the healthcare establishment devices 108 are described as existing within a healthcare establishment, examples are considered in which such devices may be found outside of a healthcare establishment, in some cases.

In examples, the patient devices 106 and/or the clinician devices 110 may include computing devices such as mobile phones, tablet computers, laptop computers, desktop computers, and the like. The patient devices 106 may be associated with the patient 102 and/or friends, family members, or associates of the patient 102, and provide these individuals with information about the health of the patient 102. Similarly, the clinician devices 110 may provide a clinician (e.g., a physician, nurse, technician, pharmacist, dentist, etc.) with information about the health of the patient 102. In some cases, the clinician devices 110 may exist within a healthcare provider establishment (e.g., alongside the healthcare establishment devices 108), although examples are also considered in which the clinician devices 110 exist and/or are transported outside of a healthcare provider establishment, such as a physician's mobile phone or home desktop computer that the physician may use when the physician is on-call.

The patient devices 106, the healthcare establishment devices 108, and/or the clinician devices 110 may include a processor, microprocessor, and/or other computing device components, shown and described below. For instance, patient devices 106, the healthcare establishment devices 108, and/or the clinician devices 110 may be configured as mobile phones, tablet computers, laptop computers, etc., to deliver or communicate patient data 116, image data 118, alerts 120, and the like amongst one another and to other devices. In some examples, one or more of the patient devices 106, the healthcare establishment devices 108, and/ or the clinician devices 110 may include or otherwise be in communication with a camera configured to capture the image data 118, which may comprise images and/or video.

The patient management system 112 may be comprised of one or more server computing devices, which may communicate with the patient devices 106, the healthcare establishment devices 108, and/or the clinician devices 110 to respond to queries, receive data, and so forth. Communication between the patient management system 112, the patient devices 106, the healthcare establishment devices 108, and/ or the clinician devices 110 occurs via the network 114, where the communication can include the patient data 116 related to the health of the patient 104, the image data 118 collected by a camera associated with the patient devices 106 and/or the clinician devices 110, the alerts 120, and so forth. A server of the patient management system 112 can act on these requests from the patient devices 106, the healthcare establishment devices 108, and/or the clinician devices 110, determine one or more responses to those queries, and respond back to the patient devices 106, the healthcare establishment devices 108, and/or the clinician devices 110. A server of the patient management system 112 may also include one or more processors, microprocessors, or other computing devices as discussed in more detail in relation to FIG. 11.

The patient management system 112 may include one or more database systems accessible by a server storing different types of information. For instance, a database can store correlations and algorithms used to manage the patient data 116 and/or the image data 118 to be shared between the patient devices 106, the healthcare establishment devices 108, and/or the clinician devices 110. A database can also include clinical data. A database may reside on a server of the patient management system 112 or on separate computing device(s) accessible by the patient management system 112.

Additionally, in some examples, the patient management system 112 may include one or more machine-learned models 122. For instance, the patient management system 112 may receive the patient data 116 and/or the image data 118 and input at least a portion of this data into the machine-learned model(s) 122. In some cases, the machine-learned models 122 may comprise a convolutional neural network, configured to output a probability of a progression of the wound 104. For instance, the machine-learned model 122 may represent future states of an entity (e.g., a wound), such as: 1) a probability distribution over the entity state space at each timestep; 2) multimodal (e.g., representing a plurality of possible progressions) to cover a diversity of possible implicit progressions an entity might follow (e.g., a rate of healing of the wound based on different levels of adherence to a treatment protocol); and 3) one-shot, meaning the ability to predict full progressions (and/or time sequences of state distributions) without iteratively applying a recurrence step.

The machine-learned model 122 may output one or more predictions associated with progression of the wound 104. For example, in the case of the wound 104, the predictions may include probabilities of progression associated with characteristics of the wound determined from the image data 116, such as a color of the wound 104, whether blistering is present with the wound 104, whether skin loss is present with the wound 104, whether eschar is present with the wound 104, a depth of the wound 104, whether fat tissue is present with the wound 104, whether muscle tissue is present with the wound 104, whether bone tissue is present with the wound 104, a granularity of the wound 104, whether pus is present with the wound 104, and so forth.

Alternatively or additionally, the predictions may include probabilities of progression associated with characteristics of the patient 102 determined from the patient data 116, such as a demographic of the patient 102 on which the wound 104 is located, a comorbidity of the patient 102, a medication being taken by the patient 104 while the wound is being observed, and so on.

In some examples, the machine-learned models 122 may comprise one or more supervised models (e.g., classification, regression, similarity, or other type of model), unsupervised models (e.g., clustering, neural network, or other type of model), and/or semi-supervised models configured to determine a classification of the wound 104. For instance, the machine-learned model 122 may be a classification model that outputs a classification of the wound based at least in part on the patient data 116 and/or the image data 118. An example classification may include whether the wound 104 is a deep tissue pressure injury (DTPI), or a wound caused by another event than DTPI. Alternatively or additionally, the machine-learned model 122 may classify whether the wound 104 has a bacteria content, and/or whether the bacteria content is Gram negative or Gram positive.

In some cases, the patient management system 112 may receive an electronic medical record (EMR) as part of the patient data 116, and associate the image data 116 with the EMR for the patient 102. The patient management system 112 may then determine a condition of the patient based at least in part on the EMR, and input the condition into the machine-learned model 122 to provide additional information to the machine-learned model for classifying the wound 104. For example, the EMR of the patient 104 may indicate immunodepression, which may cause the machine-learned model 122 to provide a classification associated with poor vascularization.

In some examples, the machine-learned model 122 may classify the wound 104 based on wound stages. Wound staging is a standardized classification having five stages, I, II, III, IV, and Unstageable. Stage I is evidenced by intact skin with non-blanchable redness of a localized area, and may be over a bony prominence. Stage II is evidenced by loss of dermis presenting as a shallow open ulcer with a red-pink wound bed or open/ruptured serum-filled blister. Stage III is evidenced by subcutaneous fat that may be visible, but bone, tendon, and/or muscle are not exposed. Stage IV is evidenced by exposed bone, tendon, and/or muscle. Unstageable wounds are evidenced by a base of the wound being covered by dead tissue.

To determine a stage of the wound 104 for the classification, the machine-learned model 122 may determine various characteristics of the wound from the image data 118. As mentioned above, the image data 118 may comprise images and/or video, where the machine-learned model 122 may determine characteristics of the wound based on frames of the video input into the machine-learned model 122. For example, the machine-learned model 122 may determine, from the image data 118, a color of the wound 104, whether blistering is present with the wound 104, whether skin loss is present with the wound 104, whether eschar is present with the wound 104, a depth of the wound 104, whether fat tissue is present with the wound 104, whether muscle tissue is present with the wound 104, whether bone tissue is present with the wound 104, a granularity of the wound 104, whether pus is present with the wound 104, and so forth. Alternatively or additionally, the machine-learned model 122 may determine, from the image data 118, one or more measurements of the wound 104 such as a length, a width, an area, a depth, or a volume of the wound, and use the measurements to classify the wound 104. In some cases, the machine-learned model 122 may receive multiple instances of image data 118 that were captured at different times, and output the classification (e.g., the stage) based at least in part on differences in characteristics of the wound between the multiple instances of image data 118 and an amount of time between the instances of image data 118 being captured. In some instances, the machine-learned model 122 may use the stage information over time to predict progression of the wound in the future, similar to the description above.

The network 114 is typically any type of wireless network or other communication network known in the art. Examples of the network 114 include the Internet, an intranet, a wide area network (WAN), a local area network (LAN), and a virtual private network (VPN), cellular network connections and connections made using protocols such as 802.11a, b, g, n and/or ac. Alternatively or additionally, the network 114 may include a nanoscale network, a near-field communication network, a body-area network (BAN), a personal-area network (PAN), a near-me area network (NAN), a campus-area network (CAN), and/or an inter-area network (IAN).

In some examples, the patient management system 112, patient devices 106, the healthcare establishment devices 108, and/or the clinician devices 110 may generate, store, and/or selectively share the patient data 116 and/or the image data 118 between one another to provide the patient 102 and/or persons assisting with treatment of the patient 102 with improved outcomes by effectively communicating information about the wound 104. In some cases, the patient devices 106 and/or the clinician devices 110 may include a healthcare application 124 to receive, generate, store, and/or share data such as the patient data 116 and/or the image data 118. In an illustrative example, the clinician device 110 may be a computing device (e.g., a mobile phone or tablet) that includes a healthcare application, which may be used by a bedside nurse to monitor a health of the patient 102 while the patient 102 is in a hospital. In some cases, the bedside nurse may not have expertise in wound care. Therefore, the healthcare application of the clinician device 110 may assist the bedside nurse with caring for the wound 104 of the patient 102 while the patient 102 is in the hospital.

For example, the bedside nurse may use a camera of the clinician device 110 to capture an image and/or video of the wound 104 as described herein, and use the healthcare application to share the image and/or video (e.g., image data 118) with other healthcare providers who may have more knowledge about wounds than the bedside nurse (e.g., a physician or WOC), to store the image data 118 in an EMR associated with the patient 102, and the like. The clinician device 110 may share the image data 118 and patient data 116 associated with the patient 102 with the patient management system 112 via the network 114. In some examples and as described in more detail below, the patient management system 112 may use machine learning and/or rules-based algorithms to analyze the image data 118 captured by the clinician device 110 and/or the patient data 116 associated with the patient 102, and may provide the bedside nurse with instructions to care for the wound 104. Alternatively or additionally, the patient management system 112 may use machine learning and/or rules-based algorithms to determine whether a physician or WOC is needed to evaluate the wound 104, and if so, may send an alert 120 that an in-person evaluation is needed to a different one of the clinician devices 110 associated with the appropriate healthcare provider.

In another illustrative example, the patient device 106 may be a computing device (e.g., a mobile phone or tablet) that includes a healthcare application, which may have at least some similar functionality to the healthcare application of the clinician device 110 referenced above. Oftentimes, the patient 102 and/or persons caring for the patient 102 outside of a healthcare establishment (e.g., friends, family members, home care nurses, physical therapists, etc.) do not have wound care expertise. Therefore, the healthcare application of the patient device 106 may assist the patient 102 and/or persons caring for the patient with wound care while the patient 102 is outside of a healthcare establishment, such as a hospital.

For instance, the patient 102 and/or persons caring for the patient may use a camera of the patient device 106 to capture an image and/or video of the wound 104 as described herein, and use the healthcare application to share the image and/or video (e.g., image data 118) with healthcare providers (e.g., a bedside nurse, a home care nurse, a physician, a WOC, etc.), to store the image data 118 in an EMR associated with the patient 102, and the like. The patient device 106 may share the image data 118 and patient data 116 associated with the patient 102 with the patient management system 112 via the network 114. In some examples and as described in more detail below, the patient management system 112 may use machine learning and/or rules-based algorithms to analyze the image data 118 captured by the patient device 106 and/or the patient data 116 associated with the patient 102, and may provide the patient 102 and/or persons caring for the patient with instructions to care for the wound 104.

Alternatively or additionally, the patient management system 112 may use machine learning and/or rules-based algorithms to determine whether a healthcare provider is needed to evaluate the wound 104, and if so, may send an alert 120 to a clinician device 110 associated with the appropriate healthcare provider that an in-person evaluation is needed, or may direct the patient 102 to go to a healthcare establishment for an evaluation. For instance, the machine-learned model 122 may determine that the wound 104 has not improved (e.g., decreased by one or more Wound Stage Classification numbers) over a predetermined time period (e.g., one day, three days, one week, two weeks, etc.) since the patient 102 has left the healthcare establishment, and based on this determination, may send the alert 120 to the clinician device 110 indicating such. The machine-learned model 122 may, in some cases, determine that the wound 104 has remained open for a predetermined amount of time (e.g., two weeks, three weeks, four weeks) since the patient 102 has left the healthcare establishment, and based on this determination, may send the alert 120 to the clinician device 110 indicating that the wound 104 has become a chronic wound. Other examples are also considered.

In some examples, the patient management system 112 may use a classification of the wound 104 provided by the machine-learned model 122 to determine an efficacy of a treatment of the wound. Treatment of the wound may correspond to one or more of medications administered to the patient 102 (e.g., orally, via injection, topically at or near the site of the wound 104, etc.), bandages applied to the wound 104, movement of the patient 102 (e.g., a frequency that the patient 102 has been turned in a hospital bed, physical therapy performed by the patient 102, a number of steps traversed by the patient 102, etc.), and so forth. The patient management system 112 may determine an efficacy of a treatment based on whether a condition of the wound 104 has improved over a time period during which the treatment was administered. For example, the patient management system 112 may determine that a Wound Stage Classification has remained the same (e.g., based on a classification of the wound 104 from the machine-learned model 122) for one week despite the patient 102 receiving a treatment of being turned in their hospital bed on a set schedule. The patient management system 112 may compare the Wound Stage Classification of the wound 104 over time to a standard indicating that with turning a patient in their hospital bed on the set schedule, the Wound Stage Classification should improve by one increment. Therefore, the patient management system 112 may determine that the efficacy of the treatment being administered for the wound 104 is insufficient.

Further, in some examples, the patient management system 112 may generate a treatment recommendation based on the determined efficacy of the treatment. The treatment recommendation may include one or more of increasing or decreasing a frequency of a treatment, adding an additional treatment to a current treatment, adding a different treatment while ceasing a current treatment, and so on. Using the example above, the patient management system 112 may generate a treatment recommendation that turning the patient 102 in the hospital bed according to the set schedule is insufficient to improve the condition of the wound 104, and an oral medication is recommended to assist with healing the wound 104. The patient management system 112 may determine that the patient 102 is currently located outside of a healthcare establishment, and deliver a treatment recommendation to the patient device 106 if the treatment recommendation is able to be administered outside of the healthcare establishment (e.g., by the patient 102).

Additionally, in some cases, the patient management system 112 may determine that the treatment recommendation is to be administered by a healthcare provider. The patient management system 112 may determine a specific caregiver type of multiple caregiver types to execute the treatment recommendation. Caregiver types may include, but are not limited to, medical assistants, bedside nurses, WOC nurses, physician assistants, primary care physicians, specialized care physicians (e.g., a Certified Wound Specialist Physician (CWSP)), and so forth. Certain treatments may require a more specialized and/or experienced caregiver to administer. For instance, a bedside nurse may be able to change a bandage covering the wound 104, but may not have experience with removing diseased tissue from the site of the wound 104. Removing diseased tissue may require the expertise of a CWSP. Accordingly, the patient management system 112 may store caregiver types with different treatment recommendations that are appropriate for administering the recommended treatment.

Once the patient management system 112 determines a caregiver type to execute the treatment recommendation, the patient management system 112 can output the treatment recommendation to a clinician device 110 associated with a caregiver of the caregiver type. For example, in the instance in which the treatment recommendation includes a bandage change on the wound 104, the patient management system 112 can output the treatment recommendation to a bedside nurse, without outputting the treatment recommendation to other caregiver types. In this way, simpler treatment recommendations can be executed by healthcare providers with less wound experience, and wound care specialists can be directed to cases in which the treatment recommendations require more expertise.

Example configurations of the patient devices 106, the healthcare establishment devices 108, and/or the clinician devices 110, the patient management system 112, and methods for their use, are shown and described with reference to at least FIGS. 2-11 below.

Figure 2:
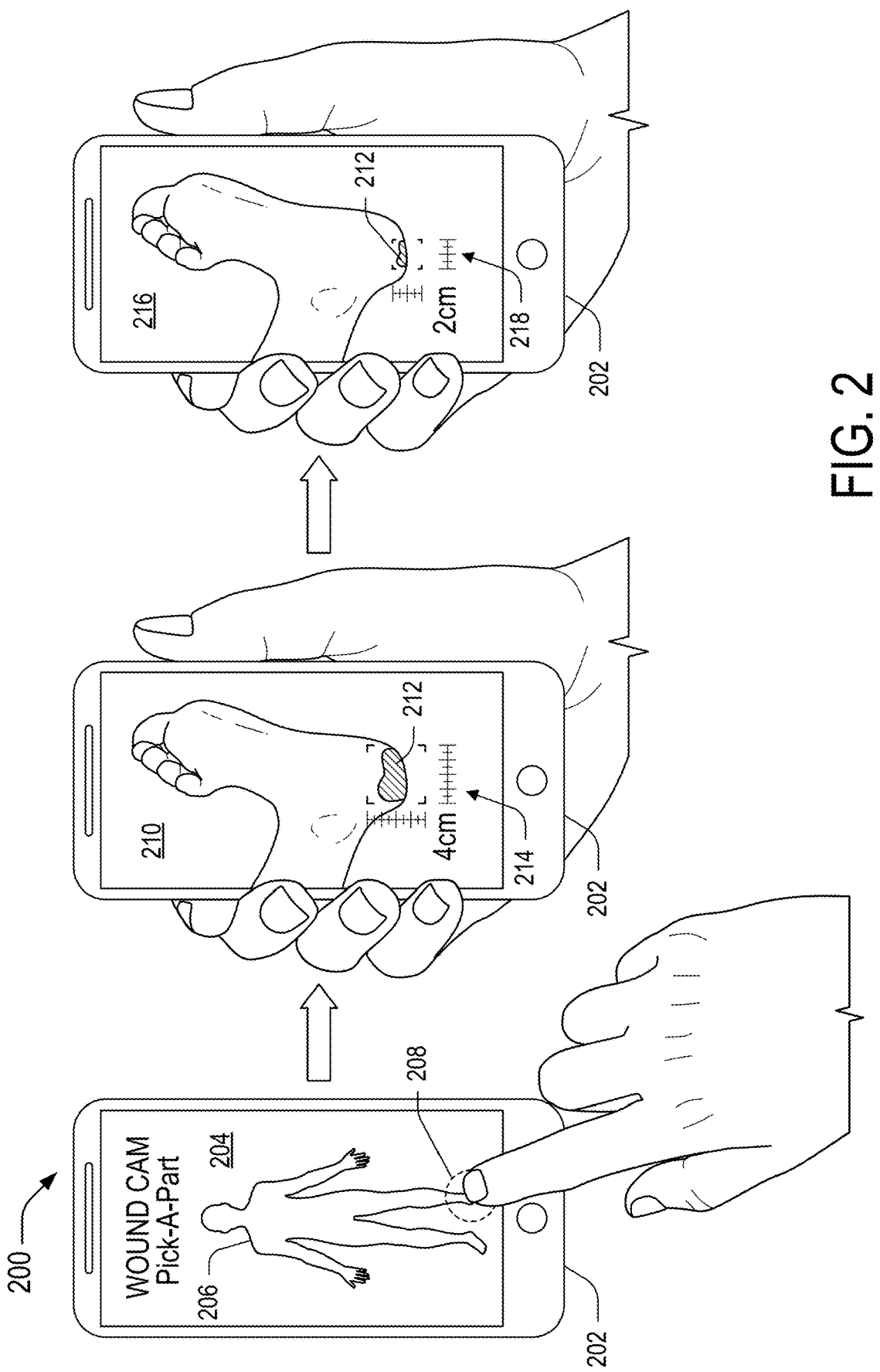
FIG. 2 is an example sequence of user interfaces used to select a body part type and capture images of a wound, in accordance with examples of the disclosure.

FIG. 2 is an example sequence 200 of user interfaces which may be used to select a body part type and capture images of a wound, in accordance with examples of the disclosure. A device 202 is shown at a first time displaying a user interface 204. The device 202 may correspond to the patient device 106 and/or the clinician device 110 described in relation to FIG. 1, and the user interface 204 may be a user interface of the healthcare application 124. Although generally described as a device having a touch interface, the device 202 may be any suitable computing device (e.g., a desktop or laptop computer), and the described operations may be performed using a keyboard, mouse, or other input technique.

The user interface 204 may be displayed in a touch interface of the device 202, enabling a user to select a body part at or near a location of a wound. The user interface 204 may include an outline 206 of a body of a person. As shown, the user has provided a touch input 208 (indicated by a dashed circle) on the outline 206 which may correspond to a location of a wound on a patient. Although not explicitly shown, after providing the touch input 208, one or more additional user interfaces may be displayed to zoom in to the location indicated by the touch input 208, to refine the position of the touch input 208, and so forth to ensure a correct representation of the body part at which the wound is located is selected. Alternatively or additionally, the user interface 204 may provide functionality that enables the user to rotate and/or move the outline 206 to ensure a correct representation of the body part at which the wound is located is selected. In some examples, and explained in more detail in relation to FIGS. 3-5, the healthcare application 124 may provide functionality to capture an image and/or a video of a wound after a body part is selected in the user interface 204.

The device 202 is shown at a second time displaying a user interface 210 of the healthcare application 124 after a body part has been selected in the user interface 204 and an image of a wound 212 has been captured, as described in more detail below. The user interface 210 includes an image of the wound 212, along with an overlay 214 on the image indicating one or more dimensions of the wound 212. In some examples, the patient management system 112 and/or the healthcare application 124 may determine dimensions of the wound 212, such as length, width, height, depth, diameter, area, and the like, based at least in part on a known relative size of the body part selected in the user interface 204. For instance, the patient management system 112 may use an average size and/or a size range of a human finger (e.g., one standard deviation from the average size) when a finger is selected in the user interface 204 to determine a dimension of the wound 212 from an image or video of the wound 212.

The device 202 is shown at a third time displaying a user interface 216 of the healthcare application 124 after the second time, where an additional image of the wound 212 has been captured at the third time. Similar to the user interface 210, the user interface 216 includes an image of the wound 212, along with an overlay 218 on the image indicating one or more dimensions of the wound 212. As shown in this example, the wound 212 has reduced in size, as evidenced by the change from the dimension indicated in the overlay 214 to the dimension indicated in the overlay 218. Oftentimes, wound progression may be difficult to determine over time, especially to persons who have not had training with wound care. Therefore, the overlay 214 and the overlay 218 provide users with metrics on how the wound 212 is progressing in the form of dimensions of the wound 212.

Figure 3:
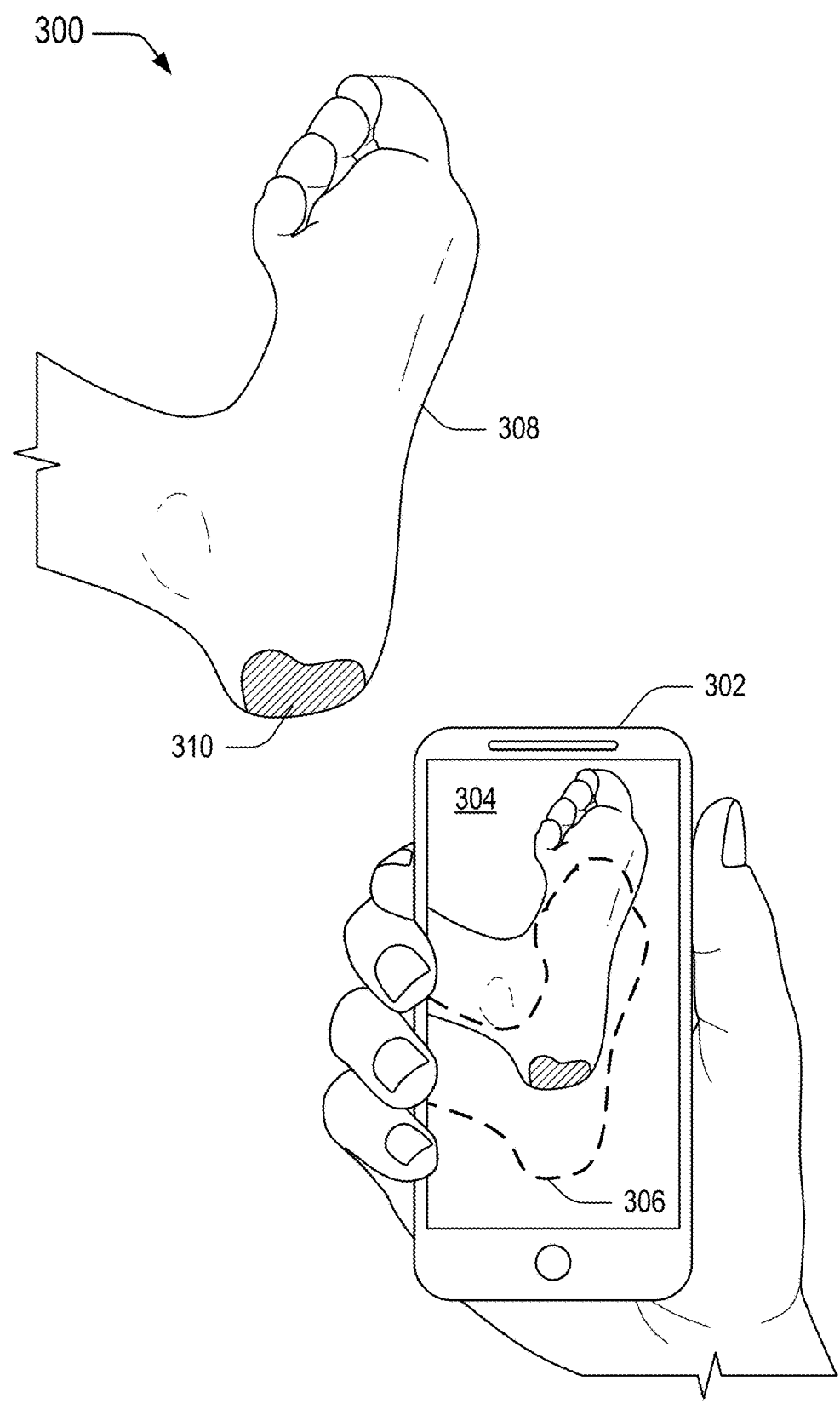
FIG. 3 is an example environment including a device displaying a camera feed and a body part type outline, in accordance with examples of the disclosure.

FIG. 3 is an example environment 300 including a device 302 displaying a camera feed 304 and a body part type outline 306, in accordance with examples of the disclosure. The device 302 may correspond to the patient device 106, the clinician device 110, and/or the device 202 described in relation to FIG. 1 and FIG. 2, and the camera feed 304 may be displayed in a user interface of the healthcare application 124. In some examples, the camera feed 304 may be displayed in response to selection of a body part from the user interface 204 as described in relation to FIG. 2. The camera feed 304 may be a live feed received from a camera of the device 302, and/or a camera remote from the device 302 (e.g., via the network 114), of a body part 308 having a wound 310. While the description of FIG. 3 generally describes capturing an image of the camera feed 304, examples are also considered in which a video of the camera feed 304 is captured using the outline 306 as well.

In some examples, the healthcare application 124 may cause the outline 306 of the body part selected in the user interface 204 to be displayed over the camera feed 304. The outline 306 may provide a user with a guide for capturing an image of the body part 308 where the wound 310 is located. In conventional systems, users would capture images of wounds at varying distances from the wounds, with no standardization to determine a distance or angle to capture the wound. When images of wounds were shared with others in conventional systems (e.g., an image captured by a bedside nurse and shared with a WOC), the user receiving the image would not be able to determine a size, severity, or characteristics of a wound, especially in images zoomed in to the wound where no reference objects were pictured for size comparison. Accordingly, by providing the outline 306 in the camera feed 304 as described herein, users can align the body part 308 of the patient with the outline 306, thus standardizing a distance of the camera from the wound 310 when an image of the wound 310 is captured. Thus, when the image of the wound 310 is shared, the receiving user can more easily determine a size, severity, or other characteristics of the wound 310.

In examples, a user may capture an image of the camera feed 304 using the outline 306 to align the body part 308 at a desired position and distance from a camera of the device 302. The patient management system 112 may receive the captured image and determine whether the image depicts a body part of the body part type selected in the user interface 204 of FIG. 2. For instance, the patient management system 112 may input the image and the selected body part type into one of the machine-learned models 122 trained to determine whether an image depicts a body part of the body part type, and receive an indication as to whether the image depicts a body part of the selected body part type.

If the patient management system 112 determines that the image does include a body part of the selected body part type, the patient management system 112 may determine a size of the body part 308 from the image and associated with the outline 306. For example, the patient management system 112 may determine a size of the body part 308 based on an average size and/or a size range of the selected body part (e.g., one standard deviation from the average size). In some cases, the patient management system 112 may generate the outline 306 based on an average size of the selected body part, and determine the size of the body part 308 based on a difference in size of the body part 308 as depicted in the image from the outline 306. For instance, the patient management system 112 may determine a location of the body part 308 in the image, and determine that the location of the body part 308 is within a threshold distance (e.g., 30 pixels, 50 pixels, 70 pixels, etc.) of the outline 306 in the image. The patient management system 112 may determine the difference between the location of the body part 308 and the outline 306 at multiple points along the outline 306 (e.g., a maximum top pixel of the outline 306, a maximum bottom pixel of the outline 306, a maximum left pixel of the outline 306, a maximum right pixel of the outline 306, etc.). If the difference between the location of the body part 308 in the image and the outline 306 is greater than the threshold distance, the patient management system 112 may prompt the user to capture another image using the outline 306, and suggest to the user to adjust the camera relative to the body part 308 to obtain better alignment with the outline 306. If the difference between the location of the body part 308 in the image and the outline 306 is less than or equal to than the threshold distance, the patient management system 112 may use the image for analysis of the wound 310.

The patient management system 112 may then determine whether the image depicts the wound 310. In some examples, the patient management system 112 may determine that the image depicts the wound 310 by providing a prompt in the user interface for the user to verify that the image depicts the wound 310. Alternatively or additionally, the patient management system 112 may determine that the image depicts the wound using the machine-learned models 124, such as using one or more object detection models to detect objects of a particular class (e.g., wounds). If the patient management system 112 determines that the image depicts the wound 310, the patient management system 112 may then determine one or more characteristics of the wound 310, as described above. In some examples, the patient management system 112 may leverage the size of the body part 308 as depicted in the image to determine a characteristic of the wound 310. For example, the patient management system 112 may determine a length, width, height, and/or depth of the wound 310 based on the estimated size of the body part 308.

Figure 4:
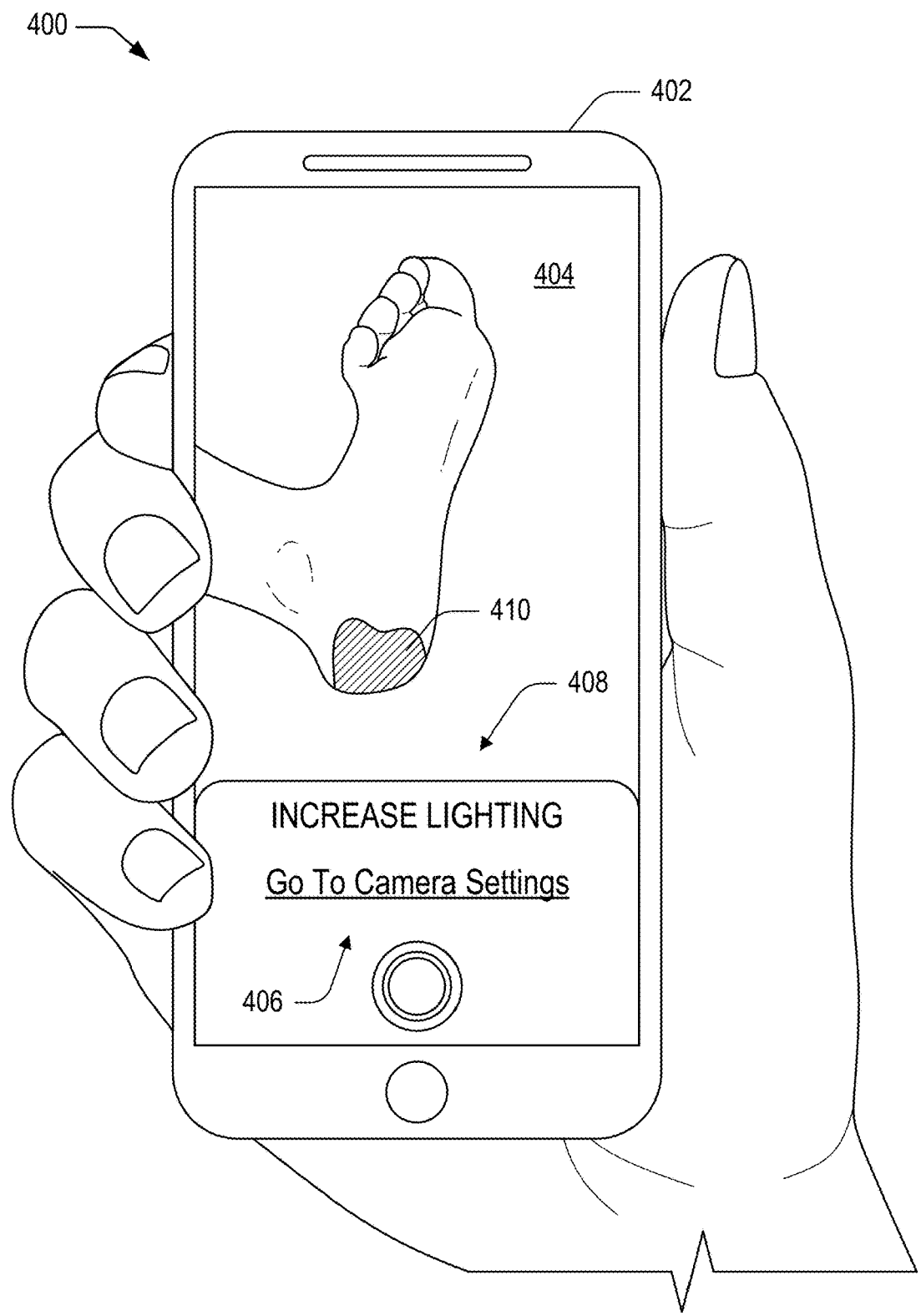
FIG. 4 is an example environment including a device displaying a camera feed and instructions to standardize the camera feed, in accordance with examples of the disclosure.

FIG. 4 is an example environment 400 including a device 402 displaying a camera feed 404 and instructions 406 to standardize the camera feed 404, in accordance with examples of the disclosure. The device 402 may correspond to the patient device 106, the clinician device 110, the device 202, and/or the device 302 described in relation to FIGS. 1-3, and the camera feed 404 may be displayed in a user interface of the healthcare application 124. In conventional systems, for example, images and videos are captured in whatever environment the patient is present in, and without regard for camera settings to compensate for light in the environment. Characteristics of a same wound may be articulated differently in two images captured at substantially the same time when lighting settings vary between the images, which may result in inconsistent analysis of the wound. Accordingly, the described techniques may standardize settings of the camera supplying the camera feed 404 to mitigate the differences that may be caused by different lighting in an environment and/or settings selected by a user.

In some examples, the healthcare application 124 may determine an illuminance, luminance, color temperature, spectral radiance, wavelength, and so forth of an environment from the camera feed 404 being received from the camera. For example, the healthcare application 124 may receive sensor data from a photocell or other light sensor of the patient device 106 and/or the clinician device 110 to extract a luminance of the environment, and/or leverage a lux meter to determine a luminance, to name a few examples. If the illumination of the environment is less than a threshold illumination (e.g., determined based on characteristics of a photocell of the patient device 106 and/or the clinician device 110, example threshold values may be 5,000 Kelvin, 5,500 Kelvin, 6,000 Kelvin, etc.), the healthcare application 124 may provide a notification 408 including the instructions 406 to increase an illumination in the environment. Additionally, in some cases, the notification 408 may include a link to go to camera settings to alter the illumination of the environment (e.g., by turning on a flash to be used when the image is captured).

The healthcare application 124 may, in some cases, match camera settings to capture a current image with camera settings used to capture previous images of a wound 410. Camera settings may include settings for one or more of aperture, shutter speed, ISO (International Standards Organization setting), and so forth, and may be stored in metadata associated with an image. In some examples, healthcare application 124 may access one or more images of the wound 410 that were previously captured, along with metadata indicating camera settings of the previously captured images. The healthcare application 124 may determine one or more settings that were used in a previously captured image, and cause a setting of the camera from which the camera feed 404 is received to match the setting to capture a new image of the wound 410. In this way, variability between different images of the wound 410 can be minimized, even when images of the wound 410 are captured with different cameras, in different environments, and/or at different times.

Figure 5:
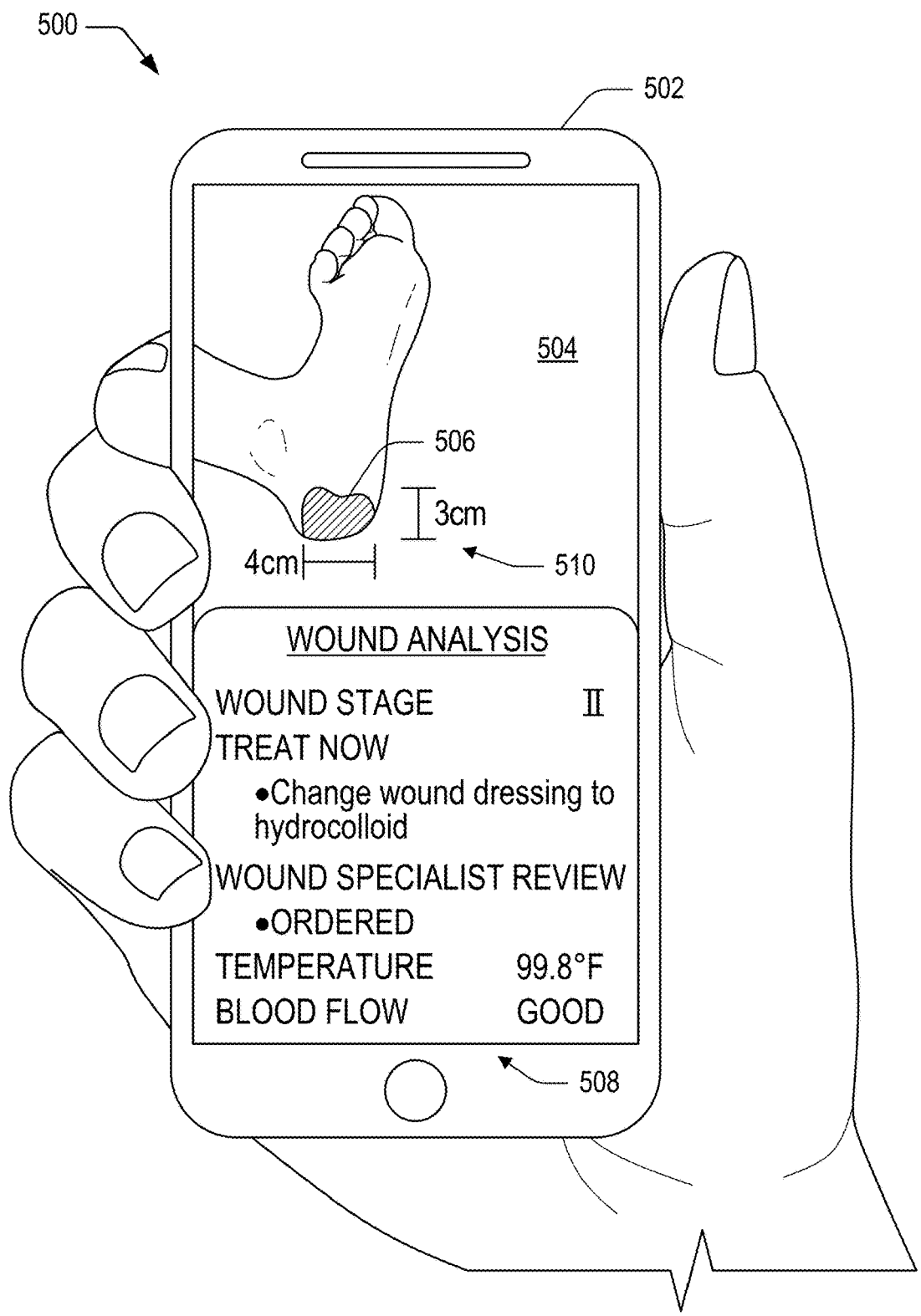
FIG. 5 is an example environment including a device displaying an image depicting a wound and information related to the wound, in accordance with examples of the disclosure.

FIG. 5 is an example environment 500 including a device 502 displaying an image 504 depicting a wound 506 and information 508 related to the wound 506, in accordance with examples of the disclosure. The device 502 may correspond to the patient device 106, the clinician device 110, the device 202, the device 302, and/or the device 402 described in relation to FIGS. 1-4, and the image 504 may be displayed in a user interface of the healthcare application 124. In some cases, the image 504 may be an image captured from the camera feed 304 and/or the camera feed 404, as described in relation to FIGS. 3 and 4.

As discussed above, the patient management system 112 may receive the image 504 of the wound 506, input the image 504 into the machine-learned model 122, and receive a classification of the wound 506 based on the image 504 from the machine-learned model 122. Examples are also considered in which the patient management system 112 receives a video having multiple frames, inputs the frames of the video into the machine-learned model 122, and receives a classification of the wound 506 based on the frames of the video from the machine-learned model 122. In examples, the patient management system 112 may provide the classification of the wound to the healthcare application 124 to be output in the user interface 504 (e.g., as part of the information 508).

As shown, the information 508 includes a Wound Stage Classification of stage II, which may be a classification received from the machine-learned model 122 of the patient management system 112. The information 508 may also include a treatment recommendation, which in the illustrated example states "Change wound dressing to hydrocolloid." As described above, the treatment recommendation included in the information 508 may be determined based on a caregiver type of a caregiver associated with the device 502.

For example, changing the wound dressing may be a suitable task for a bedside nurse to perform, and as such, the patient management system 112 may route the information 508 to the device 502 based on determining that the device 502 is associated with a bedside nurse assigned to treat the patient with the wound 506. The particular treatment recommendation illustrated in the information 508 may, in some cases, be withheld from other caregiver types, such as a surgeon who may have higher-skilled tasks to perform.

The information 508 may also indicate that a wound specialist review has been ordered. For instance, the patient management system 112 may determine that the wound 506 is not progressing towards healing at a desired rate, and based on this determination, may automatically request a WOC to analyze the wound. Alternatively, or additionally, a user of the device 502 may have a question about caring for the wound, and may use the healthcare application 124 to order a WOC to analyze the wound. When a wound specialist review is requested, either by the patient management system 112 or by a user, the image 504 and/or components of the information 508 may be delivered to the wound specialist so that the wound specialist has a context for the order prior to visiting the patient with the wound 506.

In some examples, the information 508 may include characteristics of the wound 506, such as temperature of the wound 506, blood flow to the wound 506, and so forth. The patient management system 112 may determine a temperature of the wound 506 from digital and/or thermal imaging of the wound 506 (e.g., via a thermographic camera). In some cases, the patient management system 112 may receive digital and/or thermal imaging data from a thermographic camera communicatively coupled to the patient device 106 and/or the clinician device 110 (e.g., a protective casing for the patient device 106 and/or the clinician device 110 that includes the thermographic camera). In examples, the patient management system 112 may determine blood flow to the wound 506 from a thermal image of the wound 506 based on a difference in color of an area corresponding to the wound and/or around the wound. The patient management system 112 may correlate such a difference in color in a thermal image with blood flow to the wound 506 and a state of the capillary beneath the wound 506. Additionally, the patient management system 112 may determine a size of the wound 506 as described above, and may instruct the healthcare application 124 to overlay dimensions 510 of the wound 506 on the image 504. In some examples, the patient management system 112 may use the dimensions 510 to determine the classification of the wound, by inputting the dimensions 510 into the machine-learned model 122. Additional information is also considered which may be displayed in the information 508 and/or with the image 504.

Figure 6A:
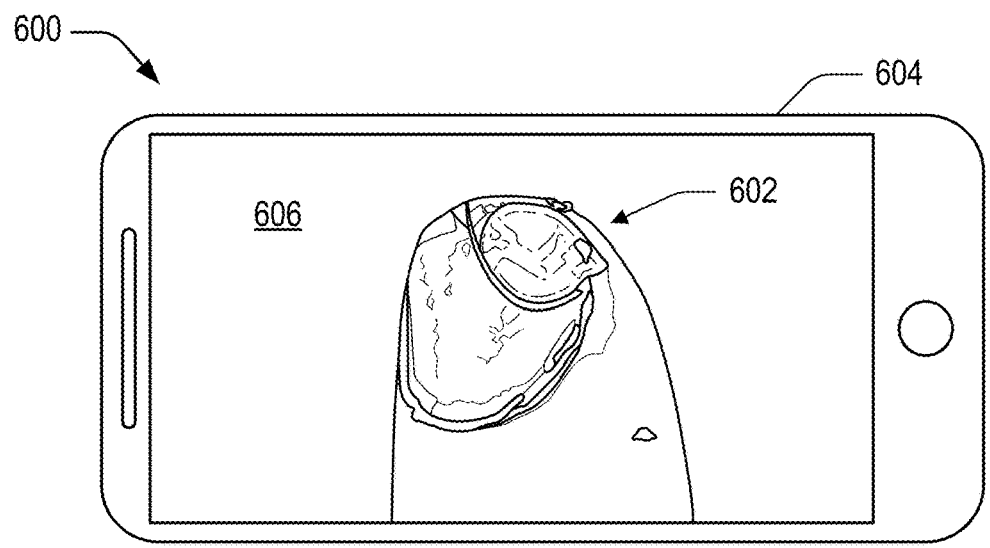
FIGS. 6A-6C are example user interfaces that depict progression of a wound over time, in accordance with examples of the disclosure.
Figure 6B:
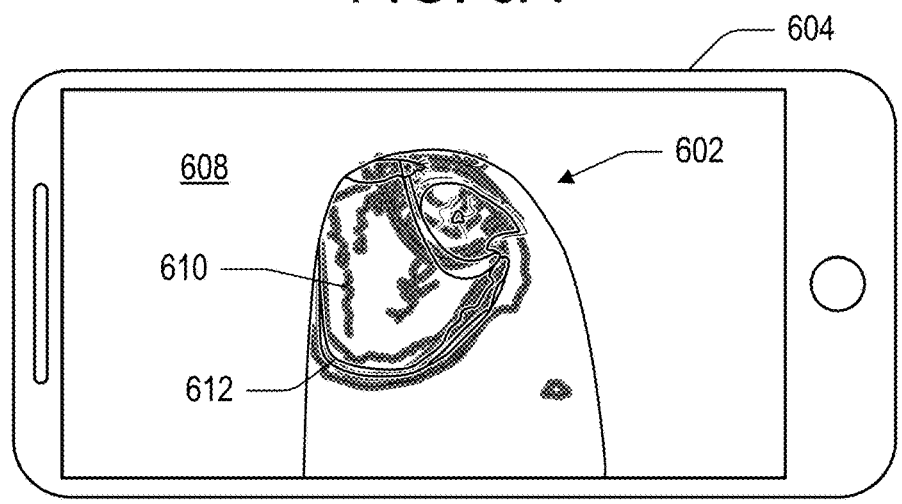
Figure 6C:
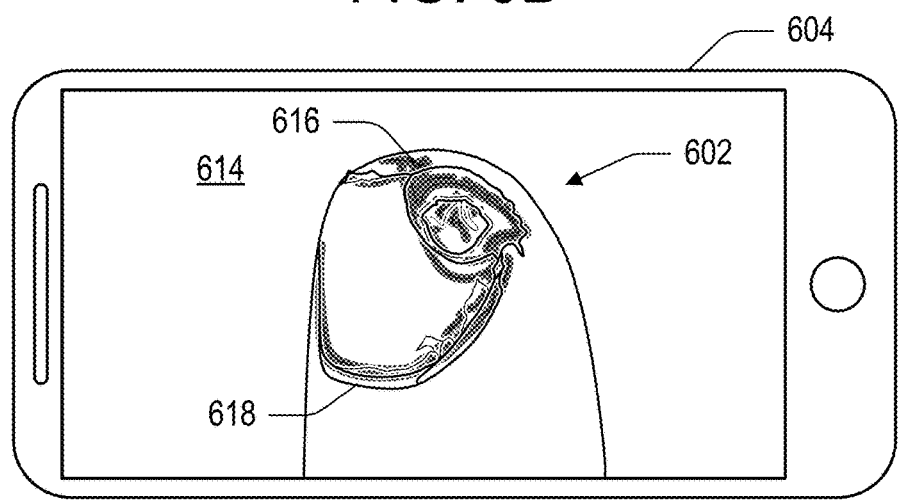

FIGS. 6A-6C are example user interfaces that depict a progression 600 of a wound 602 over time, in accordance with examples of the disclosure. For example, FIG. 6A illustrates a device 604 displaying a user interface 606 that includes an image of the wound 602 at a first time. The device 604 may correspond to the patient device 106, the clinician device 110, the device 202, the device 302, the device 402, and/or the device 502 described in relation to FIGS. 1-5, and the user interfaces described in relation to FIGS. 6A-7B that include images of the wound 602 may be user interfaces of the healthcare application 124. In some cases, the images in the user interfaces described in relation to FIGS. 6A-7B may be images captured from the camera feed 304 and/or the camera feed 404, as described in relation to FIGS. 3 and 4. In examples, the patient management system 112 may store the image displayed in the user interface 606 at least until an additional image of the wound 602 is captured at a later time.

FIG. 6B illustrates the device 604 displaying a user interface 608 that includes an image of the wound 602 at a second time after the first time illustrated in FIG. 6A. In some examples, the user interface 608 may indicate the previous image of the wound 602 taken at the first time as an overlay 610 (indicated by the thick, gray line) on the current image 612 (indicated by a thin, black line) of the wound 602. In this way, a user can see, by a visual representation of the overlay 610 and the current image 612 in the user interface 608, how the wound 602 has progressed from the first time to the second time.

Additionally, FIG. 6C illustrates the device 604 displaying a user interface 614 that includes an image of the wound 602 at a third time after the second time illustrated in FIG. 6B. In some examples, the user interface 614 may indicate the previous image of the wound 602 taken at the second time as an overlay 616 (indicated by the thick, gray line) on the current image 618 (indicated by a thin, black line) of the wound 602. The user can see, by a visual representation of the overlay 616 and the current image 618 in the user interface 614, how the wound 602 has progressed from the second time to the third time. Additionally, in some examples, the user may navigate from the user interface 614 to the user interface 608 (e.g., via a swipe gesture) to view previous progressions of the wound 602 over time.

Figure 7A:
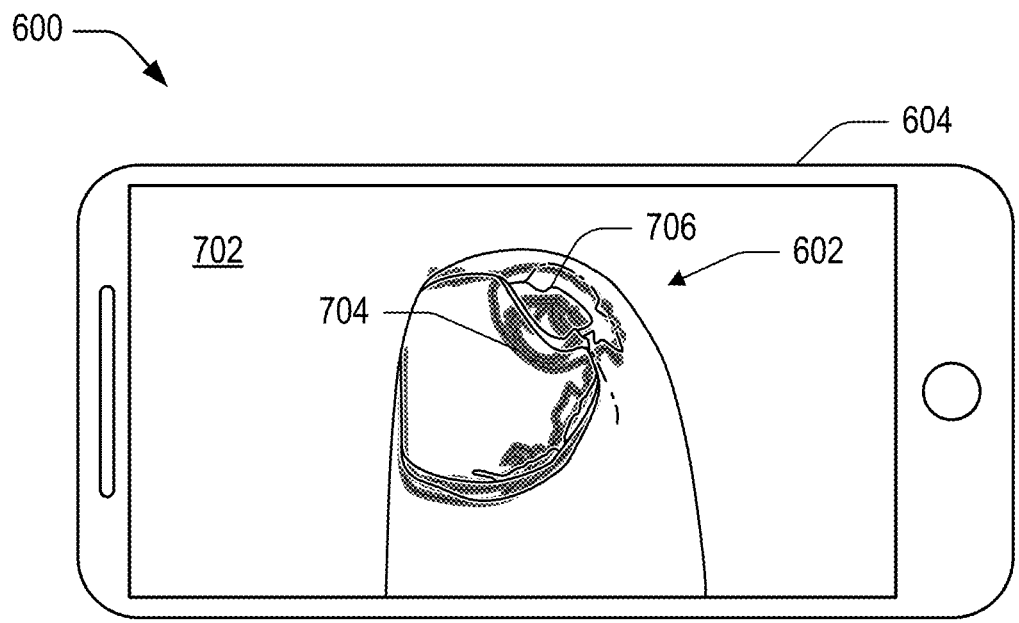
FIGS. 7A and 7B are additional example user interfaces that depict progression of a wound over time, in accordance with examples of the disclosure.
Figure 7B:
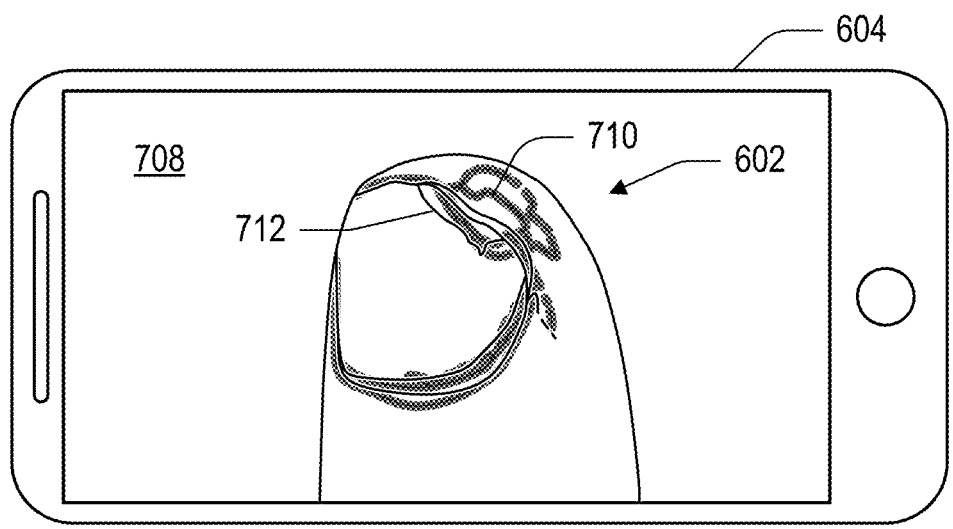

FIGS. 7A and 7B are additional example user interfaces that depict the progression 600 of the wound 602 over time, in accordance with examples of the disclosure. For instance, FIG. 7A illustrates the device 604 displaying a user interface 702 that includes an image of the wound 602 at a fourth time after the third time illustrated in FIG. 6C. In some examples, the user interface 702 may indicate the previous image of the wound 602 taken at the third time as an overlay 704 (indicated by the thick, gray line) on the current image 706 (indicated by a thin, black line) of the wound 602. The user can see, by a visual representation of the overlay 704 and the current image 706 in the user interface 702, how the wound 602 has progressed from the third time to the fourth time. Additionally, in some examples, the user may navigate from the user interface 702 to the user interface 614 and/or the user interface 608 (e.g., via a swipe gesture) to view previous progressions of the wound 602 over time.

Further, FIG. 7B illustrates the device 604 displaying a user interface 708 that includes an image of the wound 602 at a fifth time after the fourth time illustrated in FIG. 7A. In some examples, the user interface 708 may indicate the previous image of the wound 602 taken at the fourth time as an overlay 710 (indicated by the thick, gray line) on the current image 712 (indicated by a thin, black line) of the wound 602. The user can see, by a visual representation of the overlay 710 and the current image 712 in the user interface 708, how the wound 602 has progressed from the fourth time to the fifth time. Additionally, in some examples, the user may navigate from the user interface 708 to the user interface 702, the user interface 614, and/or the user interface 608 (e.g., via a swipe gesture) to view previous progressions of the wound 602 over time. While the progression 600 illustrated in FIGS. 6A-7B includes five user interfaces including images at five different times, any number of user interfaces may be used to show a progression of the wound 602 over time.

Figure 8:
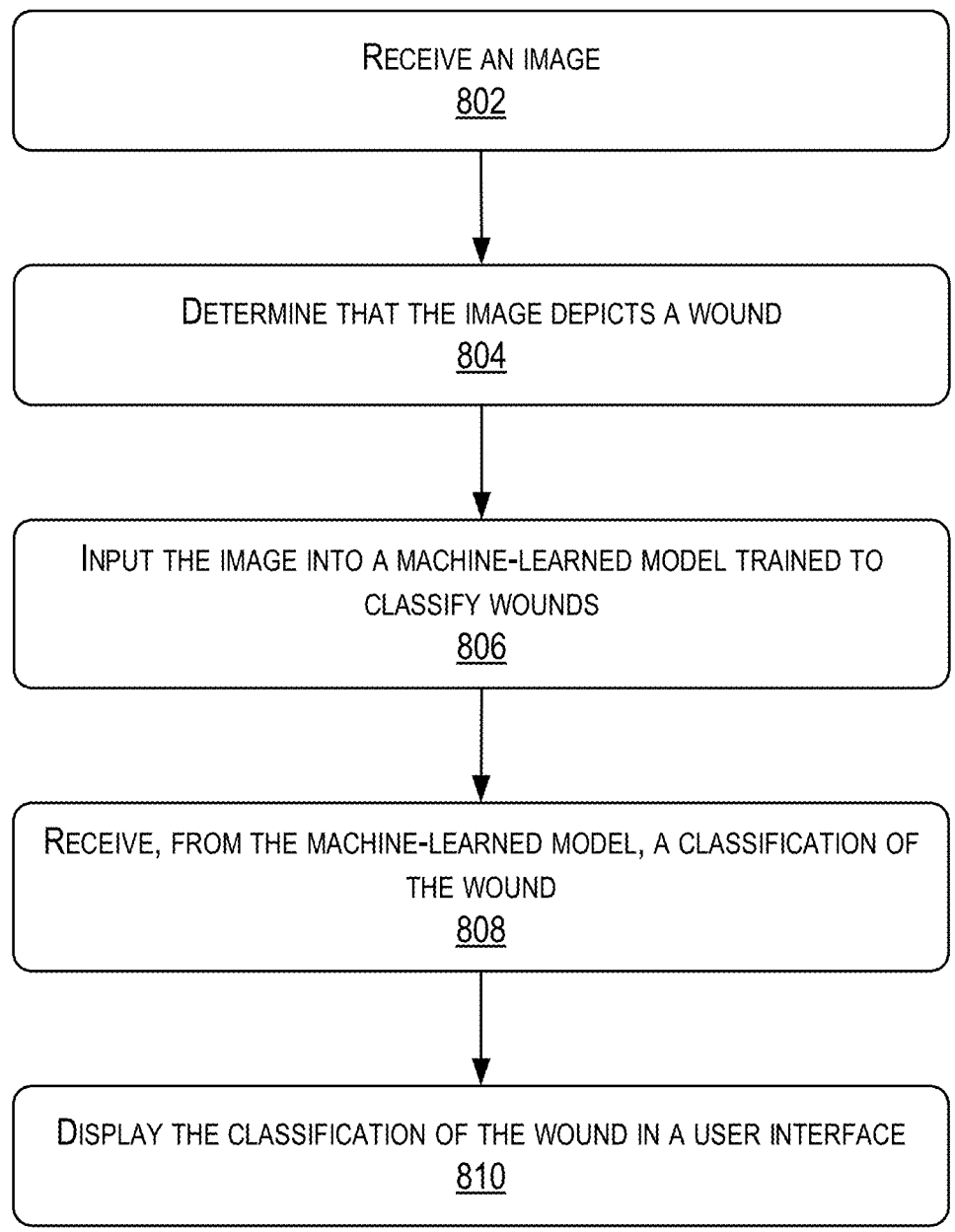
FIG. 8 is an example process for using a machine-learned model to classify a wound, according to the techniques described herein.

FIG. 8 is an example process 800 for using a machine-learned model to classify a wound, according to the techniques described herein. In some examples, one or more operations of the process 800 may be combined with one or more operations of the methods illustrated in FIG. 9 and/or FIG. 10. In some examples, the process 800 may be performed by one or more processors of computing devices, such as the patient management system 112 of FIG. 1.

At operation 802, the patient management system 112 receives an image. In some examples, the image may be included in the image data 118, which may also include metadata associated with the image such as camera settings used when the image was captured. In some cases, the image may be a frame of a video, where the patient management system 112 receives the video that includes the frame. The patient management system 112 may receive the image from the patient device 106 and/or the clinician device 110. Additionally, in some cases, the patient management system 112 may receive patient data 116 associated with the patient having the wound as well.

At operation 804, the patient management system 112 determines that the image depicts a wound. In some cases, the patient management system 112 may determine that the image depicts a wound using an object detection model to analyze the image, as described above. Other examples are also considered, such as receiving an indication of a user input from the patient device 106 and/or the clinician device 110 at a location of the wound in the image (e.g., by the user tracing an outline of the wound in a user interface of the healthcare application 124).

At operation 806, the patient management system 112 inputs the image into the machine-learned model 122, where the machine-learned model 122 is trained to classify wounds. At operation 808, the patient management system 112 receives, from the machine-learned model 122, a classification of the wound. As described above, the machine-learned models 122 may comprise one or more supervised models (e.g., classification, logistic regression, similarity, or other type of model), unsupervised models (e.g., clustering, neural network, random forest, or other type of model), and/or semi-supervised models configured to determine a classification of the wound. With a supervised model, results and/or answers from previous test may be used to gauge the accuracy of predicting new data. As stated above, unsupervised models may identify at least clusters and or at least patterns of results which don't have results and answers of prior tests and/or predictions to gauge against For instance, the machine-learned model 122 may be a classification model that outputs a classification of the wound based at least in part on the patient data 116 and/or the image data 118. Example classifications may include whether the wound is a DTPI, and/or whether the wound has bacteria content (e.g., Gram negative or Gram positive). The machine-learned model 122 may also use conditions of the patient recorded in an EMR to determine the classification of the wound.

In some examples, the machine-learned model 122 may classify the wound based on wound stages. To determine a stage of the wound for the classification, the machine-learned model 122 may determine various characteristics of the wound from the image data 118. As mentioned above, the image data 118 may comprise images and/or video, where the machine-learned model 122 may determine characteristics of the wound based on frames of the video input into the machine-learned model 122. For example, the machine-learned model 122 may determine, from the image data 118, a color of the wound, whether blistering is present with the wound, whether skin loss is present with the wound, whether eschar is present with the wound, a depth of the wound, whether fat tissue is present with the wound, whether muscle tissue is present with the wound, whether bone tissue is present with the wound, a granularity of the wound, whether pus is present with the wound, and so forth. Alternatively or additionally, the machine-learned model 122 may determine, from the image data 118, one or more measurements of the wound such as a length, a width, an area, a depth, or a volume of the wound, and use the measurements to classify the wound. In some cases, the machine-learned model 122 may receive multiple instances of image data 118 that were captured at different times, and output the classification (e.g., the stage) based at least in part on differences in characteristics of the wound between the multiple instances of image data 118 and an amount of time between the instances of image data 118 being captured.

With continued reference to operation 808, and as stated above, there may be a multitude of wound stages, going from stage 1 to stage 4. Moreover, there may be non-numeric wound stages such as a deep tissue injury ("DTI") stage, an "unstageable" stage (corresponding to, for example, a failed determination and/or prediction), and a "no pressure injury" ("NPI") stage. As another example, at operation 808 the machine-learned model 122 may utilize multiple sources of information to classify the wound to a wound stage. Example sources of information may include the images and/or video of the wound described above, general patient data, and/or specific data about the current patient who has a wound.

Concerning image characteristics of the wound, the machine-learned model 122, after being trained, whether initially or iteratively, may associate certain image characteristics with the aforementioned stages of a wound. Such image characteristics may be, for example, the color of the wound, the color of the peripheral of the wound, the thickness of skin loss, the appearance of fat tissue, the appearance of muscle, the appearance of bone or tendons, or eschar, along with the presence or absence of blistering. If a video of the wound is available, the machine-learned model 122 may determine, at operation 808, whether the wound is blanchable or non-blanchable.

In addition, at operation 808 the machine-learned model 122 may determine that if the color of the wound is the same as the surrounding skin, then there is an increased probability of the NPI wound stage. Also, after training, the machine-learned model 122 may determine that: if the color of the wound is red, such a color may indicate any of the numeric wound stages of 1, 2, 3, or 4; if the color of the wound is purple or maroon, such colors may indicate the DTI wound stage; if the color of the wound is black, such a color may indicate either the unstageable wound stage or the DTI wound stage. Additionally, if the color of the wound is black, the machine-learned model 122 may determine that such a color may indicate the numeric wound stages 3 or 4; and if the color of the wound is yellow, green, or white, such colors may indicate the numeric wound stages 2, 3, or 4.

Additionally, and in relation to the color of the peripheral wound area (discoloration around the wound for new wound development or damage to the peripheral wound area indicating lesion from dressing or nonhealing wound), at operation 808 the machine-learned model 122 may indicate that if there is no ring of color at the peripheral wound area, then the wound stage may be NPI; if the peripheral wound area is red or purple, then the wound stage may be any of the numeric wound stages between 1 to 4; if the peripheral wound area is black, then the wound stage may be any of the numeric wound stages of 2, 3, or 4; and if the peripheral wound area is white, then the wound stage may be any of the numeric wound stages of 2, 3, 4—or the non-numeric wound stages of DTI or unstageable.

Full skin loss may indicate a numeric wound stage of 2, 3, or 4; partial skin loss may indicate a numeric wound stage of 1 or 2; no skin loss may indicate the wound stage of NPI, numeric stage 1, or DTI. Concerning non limiting examples of the appearance of fat tissue in the image, correlating to a wound stage: if the appearance of fat tissue in the image of wound is present, that may indicate the numeric wound stage of 3 or 4; if fat tissue is not present in the image of the wound, that may indicate the wound stage of NPI, DTI, or unstageable—or the numeric wound stage 1 or 2. If there is an appearance of muscle present in the wound, correlating to a wound stage: the appearance of muscle present in the wound may indicate the numeric wound stage 4; if there is no appearance of muscle in the wound, then that may indicate a wound stage of NPI, stage 1, 2, or 3, DTI, or unstageable—additionally, no appearance of muscle in the wound may indicate the numeric wound stages of 1, 2, or 3.

Still in operation 808, the machine-learned model 122 may determine that an appearance of bone or tendons in a wound may indicate the numeric wound stage of 4; and no appearance of bone or tendon in a wound may indicate any of the numeric wound stages between 1 to 3—or the non-numeric wound stages of NPI, DTI, or unstageable. The presence of eschar in the wound may indicate a wound stage of unstageable; and the non-presence of eschar in the wound may indicate the non-numeric wound stages of NPI, DTI, or unstageable—or any of the numeric wound stages between 1-4. The presence of blistering in the wound may indicate numeric wound stage 1; and no presence of blistering in the wound may indicate the non-numeric wound stages of NPI, DTI, or unstageable—or any of the numeric wound stages of 1-4. A video of the wound showing that the wound is blanchable may indicate a numeric wound stage 1; and a video of the wound showing that the wound is non-blanchable may indicate the non-numeric wound stages of NPI, DTI, or unstageable—or any of the numeric wound stages of 2, 3, or 4.

As stated above, there may be EMR data concerning the wounded patient. Further, at operation 808 the machine-learned model 122 may identify EMR data that may affect the determination of the wound stage. In non-limiting examples, example EMR data that may affect the determination of wound stage may be patient age, patient weight, presence or absence of diabetes, presence or absence of pyoderma, use of vasopressors, urinary and fecal incontinence, use of a medical device, and scores such as the Braden Score, the Scott-Triggers Scale score, and the C. Munroe Scale Score. Higher age may indicate a higher risk for any of the numeric wound stages between 1 and 4. Concerning patient weight, a weight of between 0-100 lbs may indicate an increased risk for any of the numeric wound stages between 1 and 4; a weight of between 101-300 lbs may show an increased chance of the non-numeric NPI wound stage; and a weight of above 300 lbs can indicate an increased risk of having a pressure injury within any of the numeric wound stages between 1 and 4.

Still in operation 808, the machine-learned model 122 may determine that a diagnosis of diabetes or pyoderma may indicate an increased risk for any of the numeric wound stages between 1 and 4. That the use of vasopressors may indicate an increased risk of all numeric wound stages between 1 and 4, but a larger increase for numeric wound stages 3 and 4. Concerning incontinence, correlating to a wound stage: urinary incontinence may indicate the numeric wound stage 1; and fecal incontinence may indicate an increased risk of all numeric wound stages, but a larger increase for any of the numeric wound stages of 3 or 4. The use of a medical device may increase the risk of having the wound stage of DTI. The machine-learned model 122 may also determine, after training, that the different scores of a Braden Score, Scott-Triggers Scale score, or a C. Munroe Scale Score, may increase or decrease the likelihood of being in a certain stage of a wound, depending on the score result.

The machine-learned model 122 may also determine that a person's own characteristics may affect the determination of a wound stage. For example, even though the above image characteristics and general EMR data may indicate a certain stage of a wound, the machine-learned model 122 may have already stored esoteric characteristics of a specific patient, such that when a wound analysis is performed on that specific patient, the machine-learned model 122 may determine a wound stage by additionally taking into account that patient's personal characteristics.

At operation 810, the patient management system 112 causes the classification of the wound to be displayed in a user interface. For example, the patient management system 112 may provide the classification to the patient device 106 and/or the clinician device 110 to be displayed in a user interface, such as part of the information 508 describing the wound. In some cases, the patient management system 112 may output an alert 120 to a clinician device 110 along with the classification, indicating that analysis and/or treatment of the wound is requested by a particular caregiver type, as described above.

Figure 9:
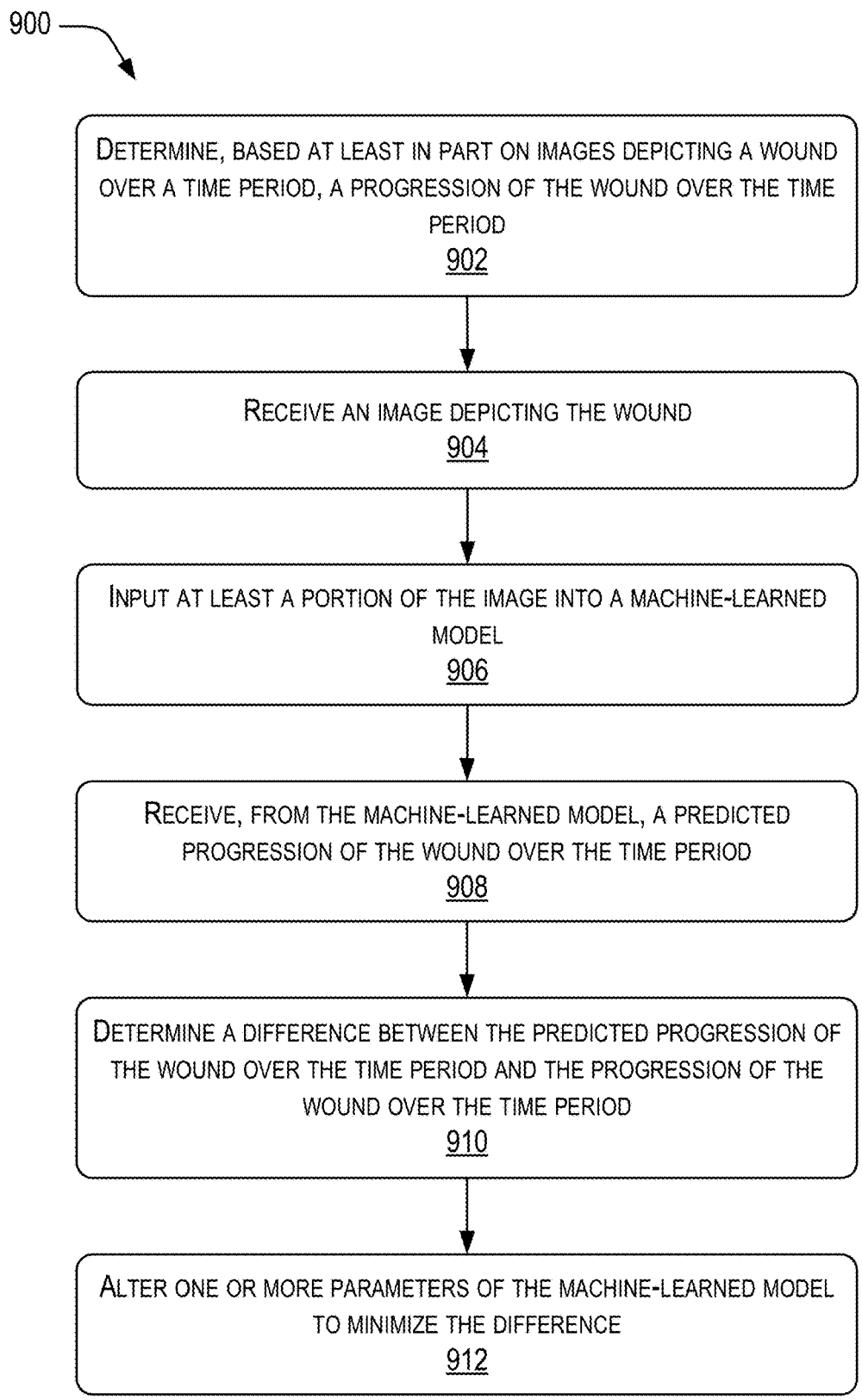
FIG. 9 is an example process for training a machine-learned model to predict a progression of a wound, according to the techniques described herein.

FIG. 9 is an example process 900 for training a machine-learned model to predict a progression of a wound, according to the techniques described herein. In some examples, one or more operations of the process 900 may be combined with one or more operations of the methods illustrated in FIG. 8 and/or FIG. 10. In some examples, the process 900 may be performed by one or more processors of computing devices, such as the patient management system 112 of FIG. 1.

At operation 902, the patient management system 112 determines, based at least in part on images depicting a wound over a time period, a progression of the wound over the time period. In some cases, the images depicting the wound over time may be received from log data comprising previously generated images, and/or may be continuously generated as the patient devices 106 and/or the clinician devices 110 provide images to the patient management system 112. In some examples, the images may depict how characteristics of the wound progress over time. The characteristics of the wound depicted in the images may be used to determine the progression of the wound, a stage of the wound, and the like. In at least some examples, multiple images depicting wounds may be annotated based on multiple classifications or with designated characteristics. Alternatively or additionally, the patient management system 112 may use data collected using other sensor modalities to determine the progression of the wound over time, such as temperature measurements, mass measurements, volume measurements, and so forth.

In some examples in which the sensor data is received from log data, determining the progression of the wound may comprise receiving a portion of the log data associated with a time the image was taken and determining the progression from the log data. For instance, determining the progression of a wound may include determining a first portion of log data generated after an image was captured, and determining a second portion of the log data generated substantially simultaneously with the image of the object. Then, the progression may be determined by comparing the first portion of the log data with the second portion of the log data. For instance, the comparison may include comparing a width or height of the wound between a first portion of the log data and a second portion of the log data, comparing a color of the wound in the first portion of the log data with a color of the wound in the second portion of the log data, determining an amount of skin loss around the wound in the first portion of the log data and an amount of skin loss around the wound in the second portion of the log data, comparing an amount of surface area or total area of the wound in a first portion and second portion of the log, and comparing a depth of the wound in a first portion of the log data and a depth of the wound in a second portion of the log data, to name a few examples.

At operation 904, the patient management system 112 receives an image depicting the wound. Similar to the discussion above, the image may be included in the image data 118, which may also include metadata associated with the image such as camera settings used when the image was captured. In some cases, the image may be a frame of a video, where the patient management system 112 receives the video that includes the frame. The patient management system 112 may receive the image from the patient device 106 and/or the clinician device 110.

At operation 906, the patient management system 112 inputs at least a portion of the image into a machine-learned model 122. In some examples, the machine-learned model 122 is a supervised model, in which the model is trained using labeled training examples to generate an inferred function to map new, unlabeled examples. Alternatively or additionally, the machine-learned model 122 trained to determine a characteristic of a wound or predicted progression of wounds may be an unsupervised model, which may identify commonalities in an input data set and may react based on the presence or absence of such commonalities in each new piece of data. In some such examples, various clustering algorithms (such as k-means) may be used to determine clusters of behaviors. As an example, where three clusters are selected, such an unsupervised model may output clusters corresponding to a wound progressing to a stage number less than a current stage, a wound progressing to a stage number greater than a current stage, or a wound maintaining a current stage.

In some cases, a dense connected convolutional neural network may be used, which may simplify the connectivity pattern between layers of the architecture. The architecture may be trained as an encoder and decoder, where the encoder may include a neural network encoder (e.g., a fully connected, convolutional, recurrent, etc.) that receives the image and outputs a tensor associated with an image feature of the image. A tensor can comprise a mathematical object analogous to but more general than a vector, wherein data is represented as an array of components that can be functions of the coordinates of a space. The architecture may also include a neural network decoder (e.g., a same type of network as the encoder, in an opposite orientation) that receives the tensor output from the encoder and outputs an image feature representation that incorporates various tensors for different image features.

According to some examples, the machine-learned model 122 may be trained using training data generated based on historical images (and/or previously generated outputs based on such historical data) from one or more perception logs or other sources of historical images. The training data may be generated by associating log data such as historical image data indicating the actual measured progression of the wound depicted in the image over time. The log data may indicate a size, color, or the like of various features of the wound, which may be used to determine a progression of the wound over time. For instance, an image depicting a wound of Wound Classification Stage III can be labeled with an actual measured length, width, height, depth, and/or subcutaneous fat that is visible at the site of the wound at the time the image was captured (e.g., as may be provided by the user inputs from manual measurements of the wound depicted in the image) and/or at a time following the time at which the image was captured. This labeling can be performed for some or all of the images depicting wounds to generate training data which can be used to train a neural network or other machine learned model, as described herein. Based on this training data, the machine-learned model 122 may be trained to detect wounds, determine classifications of wounds, and/or predict progressions of wounds, based on the wounds as captured in an image.

At operation 908, the patient management system 112 receives, from the machine-learned model 122, a predicted progression of the wound over the time period. Alternatively or additionally, the patient management system 112 may receive a classification of the wound, and/or an indication that a wound was detected in an image. In some examples, a prediction model may determine the predicted progression of the wound using one or more machine-learning models 122, such as a convolutional neural network, configured to output a probability of different possible progressions of the wound. For instance, the prediction model may represent future states of an entity, such as: 1) a probability distribution over the entity state space at each timestep; 2) multi-modal (e.g., representing a plurality of possible progressions) to cover a diversity of possible progressions the wound might take (e.g., progressing from Stage III to Stage II); and 3) one-shot, meaning the ability to predict full progressions (and/or time sequences of state distributions) without iteratively applying a recurrence step. Also, the prediction model may determine an outcome of a certain period of time, for example, whether the wound has gotten worse, better, or is stagnate after a certain period of time.

At operation 910, the patient management system 112 determines a difference between the predicted progression of the wound over the time period and the progression of the wound over the time period. Consider an example where the prediction model indicates an 80 percent chance (e.g., based on the image input into the prediction model) that a wound will progress from Stage III to Stage II within 30 days. If the measured progression of the wound is the same as the output of the machine-learned model 122, e.g., the wound progressed from Stage III to Stage II within 30 days of the image being captured, then the difference may be zero. However, if the measured progression is different from the output of the machine-learned model 122, e.g., the wound remained in Stage III, then the difference may be represented by the difference between the machine-learned model output (80 percent likelihood) and the ground truth (0), e.g., a difference of 0.8. Of course, any number of representations of progressions may be used as described elsewhere herein, and any suitable technique for representing a difference between the output of the machine-learned model 122 and the true, measured behavior may also be used without departing from the scope of the disclosure. Determining such a difference may comprise determining a cross-entropy loss, a heteroscedastic loss, or the like.

At operation 912, the patient management system 112 alters one or more parameters of the machine-learned model to minimize (or optimize) the difference (for example, by back-propagating the loss). By altering the parameters of the machine-learned model 122 to minimize the difference, the machine-learned model "learns" over time to accurately predict the progressions of wounds based on image features, along with refining classifications of wounds based on the image features. In some examples, the process may return to operation 902, to continue determining progressions of wounds, thus continuing to refine the machine-learned model to more accurately predict progressions of wounds depicted in images. Alternatively or additionally, the machine-learned model 122 may be transmitted to the patient device 106 and/or the clinician device 110 to predict and/or classify wounds based on image features.

Figure 10:
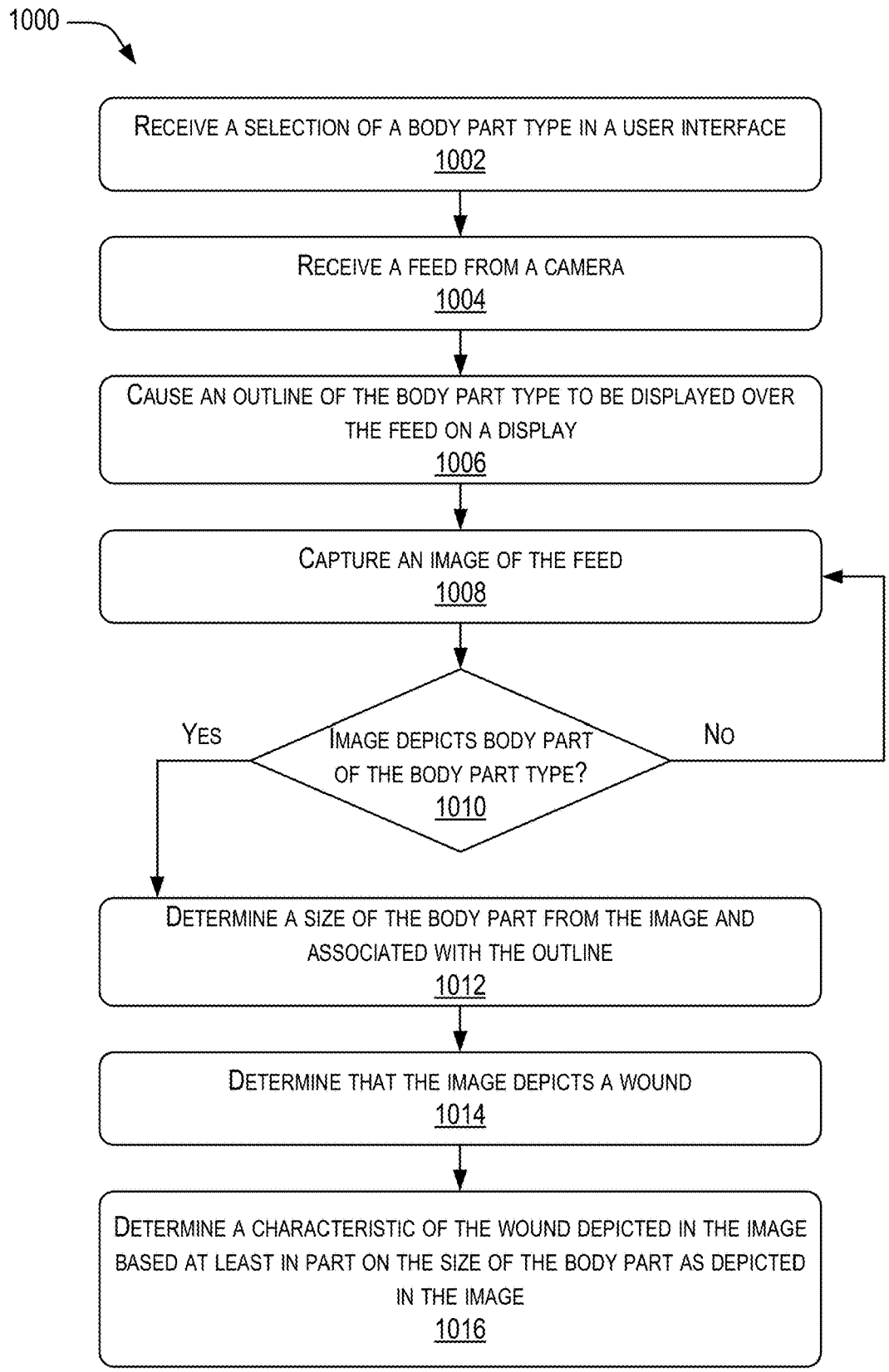
FIG. 10 is an example process for using an outline of a body part type to standardize capturing an image of a wound, and using a size of a body part of the body part type as captured in the image to determine a characteristic of the wound, according to the techniques described herein.

FIG. 10 is an example process 1000 for using an outline of a body part type to standardize capturing an image of a wound, and using a size of a body part of the body part type as captured in the image to determine a characteristic of the wound, according to the techniques described herein. In some examples, one or more operations of the process 1000 may be combined with one or more operations of the methods illustrated in FIG. 8 and/or FIG. 9. In some examples, the process 1000 may be performed by one or more processors of computing devices, such as the patient management system 112 and/or the healthcare application 124 of FIG. 1.

At operation 1002, the healthcare application 124 receives a selection of a body part type in a user interface. In some examples, the user interface of the healthcare application 124 may be displayed in a touch interface of a device, enabling a user to select a body part at or near a location of a wound. The user interface may include an outline of a body of a person, where the healthcare application 124 enables the user to rotate the outline, zoom in or out on the outline, pan to a different location of the outline, and so forth. The user may provide a touch input (and/or a different input type, such as a mouse or keyboard input) on the outline which may correspond to a location of a wound on a patient.

At operation 1004, the healthcare application 124 receives a feed from a camera. For example, the feed may be received from a camera of the patient device 106 and/or a clinician device 110. In some cases, the healthcare application 124 may cause settings of the camera from which the feed is supplied to match camera settings that were used (by the current camera or a different camera) to capture previous images of the same wound. Alternatively or additionally, the healthcare application 124 may determine that illumination of the environment depicted in the camera feed is too low or too high (e.g., by comparing to a threshold illumination), and prompt a user to alter the illumination of the environment as described above.

At operation 1006, the healthcare application 124 causes an outline of the body part type to be displayed over the feed on a display. The outline may provide a user with a guide for capturing an image of the body part where the wound is located. Accordingly, by providing the outline in the camera feed as described herein, users can align the body part of the patient with the outline to standardize a distance of the camera from the wound when an image of the wound is captured.

At operation 1008, the healthcare application 124 captures an image of the feed. In some cases, the healthcare application 124 can determine whether the body part is within a threshold distance (or distances) of the outline, and if not, may prompt the user to capture another image that depicts the body part closer to the outline.

At operation 1010, the healthcare application 124 determines whether the image depicts a body part of the body part type selected in the operation 1002. For instance, the patient management system 112 may input the image and the selected body part type into one of the machine-learned models 122 trained to determine whether an image depicts a body part of the body part type, and receive an indication as to whether the image depicts a body part of the selected body part type. The machine-learned model 122 may be an object detection model trained to detect objects and/or features of different body parts, and return an indication (e.g., yes or no) as to whether the body part depicted in the image matches features of the selected body part type.

If the healthcare application 124 determines that the image does not depict a body part of the body part type (e.g., "No" at operation 1010), the process 1000 may return to the operation 1008, in which the healthcare application 124 captures another image of the feed. In some cases, the healthcare application 124 may indicate that the image does not depict a body part of the body part type if a border of the body part in the image is greater than a threshold distance from the outline of the selected body part, as described above. In examples, the healthcare application 124 may prompt a user to capture an additional image of the selected body part that aligns more closely with the outline in response to determining that the image does not depict a body part of the body part type.

If the healthcare application 124 determines that the image depicts a body part of the body part type (e.g., "Yes" at operation 1010), the process 1000 may proceed to an operation 1012, in which the healthcare application 124 determines a size of the body part from the image and associated with the outline. For example, the patient management system 112 may determine a size of the body part 308 based on an average size and/or a size range of the selected body part (e.g., one standard deviation from the average size). In some cases, the healthcare application 124 may generate the outline based on an average size of the selected body part, and determine the size of the body part based on a difference in size of the body part as depicted in the image from the outline.

At operation 1014, the healthcare application 124 determines that the image depicts a wound. In some cases, the patient management system 112 may determine that the image depicts a wound using an object detection model to analyze the image, as described above. Other examples are also considered, such as receiving an indication of a user input from the patient device 106 and/or the clinician device 110 at a location of the wound in the image (e.g., by the user tracing an outline of the wound in a user interface of the healthcare application 124).

At operation 1016, the healthcare application 124 determines a characteristic of the wound depicted in the image based at least in part on the size of the body part as depicted in the image. In some examples, the patient management system 112 may leverage the size of the body part as depicted in the image to determine a characteristic of the wound. For example, the patient management system 112 may determine a length, width, height, and/or depth of the wound based on the estimated size of the body part.

Example System and Device

Figure 11:
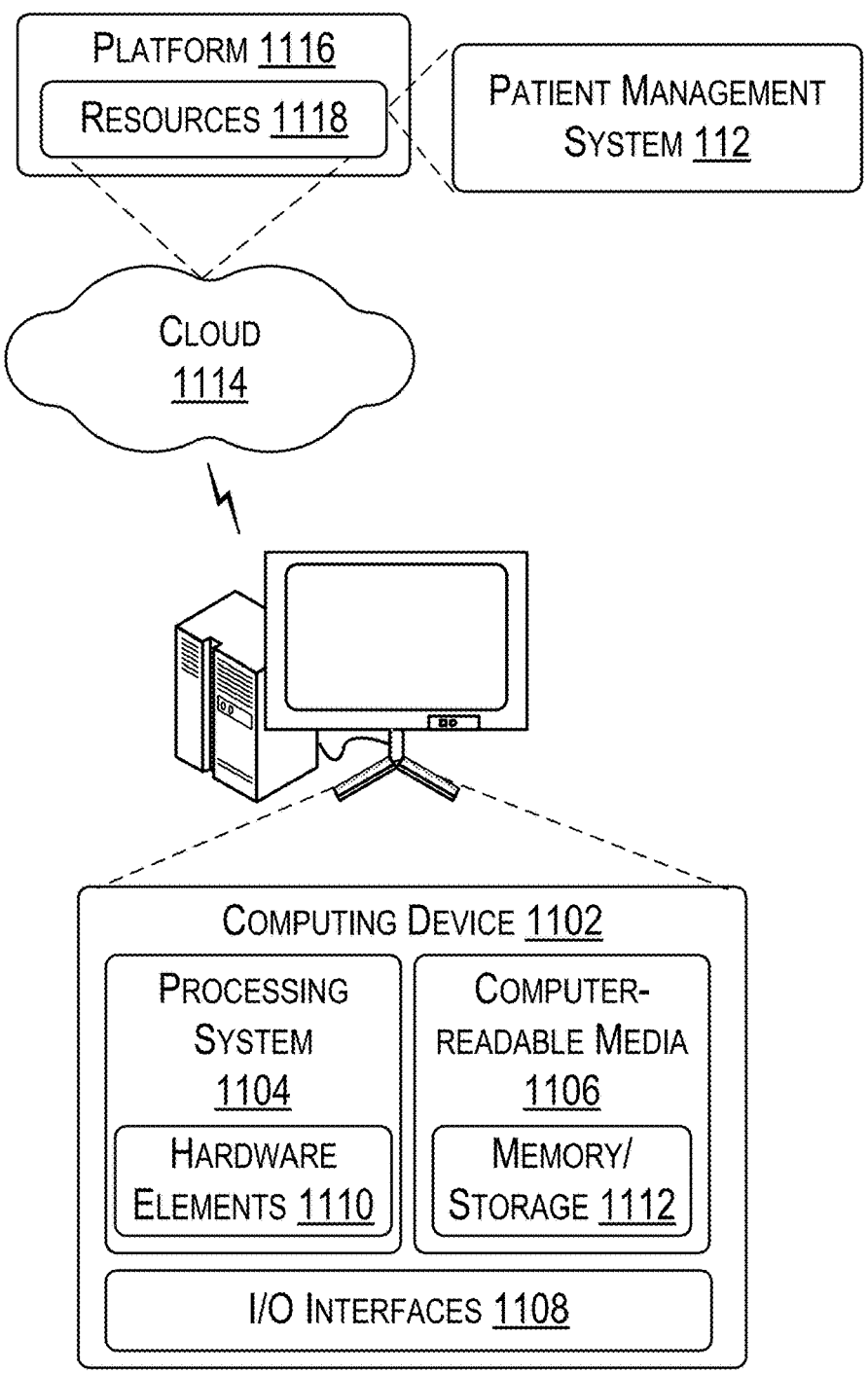
FIG. 11 depicts an example computing system and device which may be used to implement the described techniques.

FIG. 11 illustrates an example system generally at 1100 that includes an example computing device 1102 that is representative of one or more computing systems and/or devices that may implement the various techniques described herein. This is illustrated through inclusion of the patient management system 112. The computing device 1102 may be, for example, a server of a service provider, a device associated with a client (e.g., a client device), an on-chip system, and/or any other suitable computing device or computing system.

The example computing device 1102 as illustrated includes a processing system 1104, one or more computer-readable media 1106, and one or more I/O interface 1108 that are communicatively coupled, one to another. Although not shown, the computing device 1102 may further include a system bus or other data and command transfer system that couples the various components, one to another. A system bus can include any one or combination of different bus structures, such as a memory bus or memory controller, a peripheral bus, a universal serial bus, and/or a processor or local bus that utilizes any of a variety of bus architectures. A variety of other examples are also contemplated, such as control and data lines.

The processing system 1104 is representative of functionality to perform one or more operations using hardware. Accordingly, the processing system 1104 is illustrated as including hardware element 1110 that may be configured as processors, functional blocks, and so forth. This may include implementation in hardware as an application specific integrated circuit or other logic device formed using one or more semiconductors. The hardware elements 1110 are not limited by the materials from which they are formed or the processing mechanisms employed therein. For example, processors may be comprised of semiconductor(s) and/or transistors (e.g., electronic integrated circuits (ICs)). In such a context, processor-executable instructions may be electronically-executable instructions.

The computer-readable media 1106 is illustrated as including a memory/storage component 1112. The memory/storage component 1112 represents memory/storage capacity associated with one or more computer-readable media. The memory/storage component 1112 may include volatile media (such as random access memory (RAM)) and/or nonvolatile media (such as read only memory (ROM), Flash memory, optical disks, magnetic disks, and so forth). The memory/storage component 1112 may include fixed media (e.g., RAM, ROM, a fixed hard drive, and so on) as well as removable media (e.g., Flash memory, a removable hard drive, an optical disc, and so forth). The computer-readable media 1106 may be configured in a variety of other ways as further described below.

Input/output interface(s) 1108 are representative of functionality to allow a user to enter commands and information to computing device 1102, and also allow information to be presented to the user and/or other components or devices using various input/output devices. Examples of input devices include a keyboard, a cursor control device (e.g., a mouse), a microphone, a scanner, touch functionality (e.g., capacitive or other sensors that are configured to detect physical touch), a camera (e.g., which may employ visible or non-visible wavelengths such as infrared frequencies to recognize movement as gestures that do not involve touch), and so forth. Examples of output devices include a display device (e.g., a monitor or projector), speakers, a printer, a network card, tactile-response device, and so forth. Thus, the computing device 1102 may be configured in a variety of ways as further described below to support user interaction.

Various techniques may be described herein in the general context of software, hardware elements, or program modules. Generally, such modules include routines, programs, objects, elements, components, data structures, and so forth that perform particular tasks or implement particular abstract data types. The terms "module," "functionality," "logic," and "component" as used herein generally represent software, firmware, hardware, or a combination thereof. The features of the techniques described herein are platform-independent, meaning that the techniques may be implemented on a variety of commercial computing platforms having a variety of processors.

An implementation of the described modules and techniques may be stored on and/or transmitted across some form of computer-readable media. The computer-readable media may include a variety of media that may be accessed by the computing device 1102. By way of example, and not limitation, computer-readable media may include "computer-readable storage media" and "computer-readable transmission media."

"Computer-readable storage media" may refer to media and/or devices that enable persistent and/or non-transitory storage of information in contrast to mere signal transmission, carrier waves, or signals per se. Thus, computer-readable storage media refers to non-signal bearing media. The computer-readable storage media includes hardware such as volatile and non-volatile, removable and non-removable media and/or storage devices implemented in a method or technology suitable for storage of information such as computer-readable instructions, data structures, program modules, logic elements/circuits, or other data. Examples of computer-readable storage media may include, but are not limited to, RAM, ROM, EEPROM, flash memory or other memory technology, CD-ROM, digital versatile disks (DVD) or other optical storage, hard disks, magnetic cassettes, magnetic tape, magnetic disk storage or other magnetic storage devices, or other storage device, tangible media, or article of manufacture suitable to store the desired information and which may be accessed by a computer.

"Computer-readable transmission media" may refer to a medium that is configured to transmit instructions to the hardware of the computing device 1102, such as via a network. Computer-readable transmission media typically may transmit computer-readable instructions, data structures, program modules, or other data in a modulated data signal, such as carrier waves, data signals, or other transport mechanism. Computer-readable transmission media also include any information delivery media. The term "modulated data signal" means a signal that has one or more of its characteristics set or changed in such a manner as to encode information in the signal. By way of example, and not limitation, computer-readable transmission media include wired media such as a wired network or direct-wired connection, and wireless media such as acoustic, radio frequency (RF), infrared, and other wireless media.

As previously described, hardware elements 1110 and computer-readable media 1106 are representative of modules, programmable device logic and/or device logic implemented in a hardware form that may be employed in some examples to implement at least some aspects of the techniques described herein, such as to perform one or more instructions. Hardware may include components of an integrated circuit or on-chip system, an application-specific integrated circuit (ASIC), a field-programmable gate array (FPGA), a complex programmable logic device (CPLD), and other implementations in silicon or other hardware. In this context, hardware may operate as a processing device that performs program tasks defined by instructions and/or logic embodied by the hardware as well as a hardware utilized to store instructions for execution, e.g., the computer-readable storage media described previously.

Combinations of the foregoing may also be employed to implement various techniques described herein. Accordingly, software, hardware, or executable modules may be implemented as one or more instructions and/or logic embodied on some form of computer-readable storage media and/or by one or more hardware elements 1110. The computing device 1102 may be configured to implement particular instructions and/or functions corresponding to the software and/or hardware modules. Accordingly, implementation of a module that is executable by the computing device 1102 as software may be achieved at least partially in hardware, e.g., through use of computer-readable storage media and/or hardware elements 1110 of the processing system 1104. The instructions and/or functions may be executable/operable by one or more articles of manufacture (for example, one or more computing devices 1102 and/or processing systems 1104) to implement techniques, modules, and examples described herein.

The techniques described herein may be supported by various configurations of the computing device 1102 and are not limited to the specific examples of the techniques described herein. This functionality may also be implemented all or in part through use of a distributed system, such as over a "cloud" 1114 via a platform 1116 as described below.

The cloud 1114 includes and/or is representative of a platform 1116 for resources 1118. The platform 1116 abstracts underlying functionality of hardware (e.g., servers) and software resources of the cloud 1114. The resources 1118 may include applications and/or data that can be utilized while computer processing is executed on servers that are remote from the computing device 1102. Resources 1118 can also include services provided over the Internet and/or through a subscriber network, such as a cellular or Wi-Fi network.

The platform 1116 may abstract resources and functions to connect the computing device 1102 with other computing devices. The platform 1116 may also be scalable to provide a corresponding level of scale to encountered demand for the resources 1118 that are implemented via the platform 1116. Accordingly, in an interconnected device example, implementation of functionality described herein may be distributed throughout multiple devices of the system 1100. For example, the functionality may be implemented in part on the computing device 1102 as well as via the platform 1116 which may represent a cloud computing environment, such as the cloud 1114.

The example systems and methods of the present disclosure overcome various deficiencies of known prior art devices. Other examples of the present disclosure will be apparent to those skilled in the art from consideration of the specification and practice of the disclosure contained herein. It is intended that the specification and examples be considered as example only, with a true scope and spirit of the present disclosure being indicated by the following claims.

What is claimed is:

1. A method comprising:
   receiving, by a processor, an image captured by a capture device;
   identifying, by the processor, a particular body part depicted in the image and a wound associated with the particular body part;
   determining, by the processor and executing a machine-learned model using the image, a classification of the wound indicating the wound comprises a deep pressure injury, the machine-learned model being trained based on training data associated with wounded body parts matching the particular body part;
   generating, by the processor and based at least in part on the classification of the wound, a treatment recommendation comprising wound care instructions, the treatment recommendation being tailored to a caregiver of a first caregiver type;
   causing, by the processor, the classification of the wound and the treatment recommendation to be provided in a user interface rendered by a display device operably connected to the processor, the display device being associated with the first caregiver type;
   preventing, by the processor, the treatment recommendation from being provided to a caregiver of a second caregiver type;
   determining, by the processor and based on the image, that an in-person evaluation of the wound is needed;
   determining, by the processor, a second computing device associated with a physician specialized in evaluating the wound; and
   causing, by the processor, an alert requesting the physician evaluate the wound to be provided to a second user interface of the second computing device for display.

2. The method of claim 1, wherein the classification includes first information indicating that the wound has a bacteria content, and second information indicating that the bacteria content is at least one of Gram negative or Gram positive.

3. The method of claim 1, further comprising:
   receiving, by the processor, an electronic medical record (EMR) associated with a patient;
   determining, by the processor, a condition of the patient based at least in part on the EMR; and
   inputting the condition of the patient into the machine-learned model,
   wherein the classification of the wound is determined by the machine-learned model based at least in part on the condition of the patient.

4. The method of claim 3, further comprising:
   receiving, by the processor, a prediction of progression of the wound determined by the machine-learned model based at least in part on the image and the condition of the patient; and
   causing, by the processor, the prediction of the progression of the wound to be provided in the user interface rendered by the display device operably connected to the processor, the prediction of the progression of the wound comprising a plurality of predicted progressions corresponding to respective adherence to treatment protocols.

5. The method of claim 1, wherein the classification includes information indicating a stage of the wound, and wherein the stage of the wound is determined by the machine-learned model based at least in part on at least one of:
   a color of the wound;
   whether blistering is present with the wound;
   whether skin loss is present with the wound;
   whether eschar is present with the wound;
   a depth of the wound;
   whether fat tissue is present with the wound;
   whether muscle tissue is present with the wound;
   whether bone tissue is present with the wound;
   a granularity of the wound; or
   whether pus is present with the wound.

6. The method of claim 1, further comprising:
   determining, by the processor, a characteristic of the wound, the characteristic comprising a length, a width, an area, a depth, or a volume of the wound; and inputting the characteristic of the wound into the machine-learned model,
wherein the classification of the wound is determined by the machine-learned model based on the characteristic of the wound.

7. The method of claim 1, wherein the image comprises a first image received at a first time, the method further comprising:
receiving, by the processor, a second image at a second time different than the first time;
determining, by the processor, that the second image depicts the wound; and
inputting, by the processor, the second image into the machine-learned model,
wherein the classification of the wound is determined by the machine-learned model based on the second image and an amount of time from the first time to the second time.

8. The method of claim 7, further comprising:
receiving, by the processor, a predicted progression of the wound determined by the machine-learned model based at least in part on a first classification, a second classification, and the amount of time from the first time to the second time; and
causing the predicted progression of the wound to be provided in the user interface rendered by the display device.

9. The method of claim 1, further comprising:
determining, by the processor and based at least in part on the classification, an efficacy of a treatment of the wound; and
generating, by the processor, the treatment recommendation based at least in part on the efficacy of the treatment.

10. The method of claim 1, further comprising:
determining, by the processor, that the display device is associated with the caregiver of the first caregiver type and that the caregiver is available to provide a treatment included in the treatment recommendation; and
providing, by the processor, the treatment recommendation to the display device based at least in part on determining that the display device is associated with the caregiver of the first caregiver type.

11. The method of claim 1, wherein:
the image comprises a frame of a video,
inputting the image into the machine-learned model further comprises inputting the video into the machine-learned model, and
the classification of the wound received from the machine-learned model is further based on the wound as represented in the video.

12. The method of claim 1, wherein: the caregiver comprises a nurse, and wherein the physician corresponds to a third caregiver of a third caregiver type.

13. A computing device comprising:
one or more processors; and
one or more computer-readable media storing instructions that, when executed by the one or more processors, cause the one or more processors to perform operations comprising:
presenting, via a user interface of the computing device, a visual representation of a plurality of body parts;
receiving, via the user interface, first user input comprising a selection of a particular body part type of the plurality of body parts that includes a wound;
receiving a feed from a camera;
causing an outline of the selected particular body part type to be displayed over the feed on the display;
capturing an image of the feed;
determining that the image depicts a body part of the selected particular body part type;
determining a size of the body part from the image and based on the outline;
determining that the image depicts the wound on the body part of the selected particular body part type based on:
presenting, via the display, a prompt requesting second user input to verify the particular body part type in the image depicts the wound; and
receiving the second user input verifying the image depicts the wound;
determining a classification of the wound as a deep pressure injury; and
determining a characteristic of the wound depicted in the image using the size of the body part as depicted in the image.

14. The computing device of claim 13, wherein the classification includes first information indicating that the wound has a bacteria content, and second information indicating that the bacteria content is at least one of Gram negative or Gram positive.

15. The computing device of claim 13, the operations further comprising:
determining a treatment recommendation based on the classification of the wound;
determining a caregiver type of multiple caregiver types to execute the treatment recommendation, the caregiver type being specialized in a type of treatment included in the treatment recommendation;
determining a second computing device associated with a caregiver of the caregiver type; and
providing the treatment recommendation to the second computing device based on determining that the second computing device is associated with the caregiver of the caregiver type.

16. A system comprising:
a camera;
a display;
one or more processors; and
one or more computer-readable media storing instructions that, when executed by the one or more processors, cause the one or more processors to perform operations comprising:
presenting, via a user interface of the display, a visual representation of a plurality of body parts;
receiving, via the user interface, first user input comprising a selection of a particular body part type of the plurality of body parts that includes a wound;
receiving a feed from the camera;
causing an outline of the selected particular body part type to be displayed over the feed on the display;
capturing an image of the feed;
determining that the image depicts a body part of the selected particular body part type;
determining a size of the body part from the image and associated with the outline;
determining that the image depicts the wound on the body part of the selected particular body part type based on:
presenting, via the display, a prompt requesting second user input to verify the particular body part type in the image depicts the wound; and
receiving the second user input verifying the image depicts the wound;

determining a classification of the wound as a deep pressure injury; and determining a characteristic of the wound depicted in the image using the size of the body part as depicted in the image.

17. The system of claim 16, wherein determining that the image depicts the body part of the selected particular body part type further comprises:

determining a location of the body part in the image; and determining that the location of the body part is within a threshold distance of the outline in the image, wherein determining the size of the body part is based at least in part on the location of the body part being within the threshold distance.

18. The system of claim 16, the operations further comprising:

determining an illumination of an environment from the feed from the camera;

determining that the illumination of the environment is less than a threshold illumination; and providing a notification on the display to increase the illumination of the environment.

19. The system of claim 16, wherein the image is a first image and the camera is a first camera, the operations further comprising:

receiving a second image depicting the wound, the second image captured prior to the first image with a second camera;

determining, from image data associated with the second image, a first setting of the second camera used to capture the second image; and causing a second setting of the first camera to match the first setting of the second camera, wherein capturing the first image of the feed comprises using the second setting to capture the first image.

20. The system of claim 16, wherein the characteristic comprises one or more of:

a color of the wound;

whether blistering is present with the wound;

whether skin loss is present with the wound;

whether eschar is present with the wound;

a depth of the wound;

whether fat tissue is present with the wound;

whether muscle tissue is present with the wound;

whether bone tissue is present with the wound;

a granularity of the wound; or whether pus is present with the wound.

\* \* \* \* \*